US009667889B2

(12) United States Patent
Rothberg

(10) Patent No.: US 9,667,889 B2
(45) Date of Patent: May 30, 2017

(54) PORTABLE ELECTRONIC DEVICES WITH INTEGRATED IMAGING CAPABILITIES

(71) Applicant: Butterfly Network, Inc., Guilford, CT (US)

(72) Inventor: Noah Zachary Rothberg, Guilford, CT (US)

(73) Assignee: Butterfly Network, Inc., Guilford, CT (US)

( * ) Notice: Subject to any disclaimer, the term of this patent is extended or adjusted under 35 U.S.C. 154(b) by 269 days.

(21) Appl. No.: 13/856,252

(22) Filed: Apr. 3, 2013

(65) Prior Publication Data

US 2014/0300720 A1    Oct. 9, 2014

(51) Int. Cl.
*H04N 5/30* (2006.01)
*A61B 8/00* (2006.01)
(Continued)

(52) U.S. Cl.
CPC ............. *H04N 5/30* (2013.01); *A61B 8/4411* (2013.01); *A61B 8/4427* (2013.01);
(Continued)

(58) Field of Classification Search
CPC .......... G06T 7/0012; A61B 1/042; H04N 5/30
See application file for complete search history.

(56) References Cited

U.S. PATENT DOCUMENTS 4,074,564 A    2/1978 Anderson
4,075,883 A    2/1978 Glover
(Continued)

FOREIGN PATENT DOCUMENTS

AU    2003261073 A1    12/2003
AU    2003297650 A1    7/2004
(Continued)

OTHER PUBLICATIONS

Agarwal et al., Single-Chip Solution for Ultrasound Imaging Systems: Initial Results. 2007 IEEE Ultrasonics Symposium. Oct. 1, 2007;1563-6.
(Continued)

*Primary Examiner* — Zhubing Ren
(74) *Attorney, Agent, or Firm* — Mintz Levin Cohn Ferris Glovsky and Popeo, P.C.

(57) ABSTRACT

A portable electronic device (e.g., smart phone or tablet computer) is provided for generating and displaying images (e.g., 2-dimensional or 3-dimensional images) of an imaging target such as a human body. The portable electronic device may include imaging elements configured to receive radiation signals transmitted through and/or reflected by the imaging target, an imaging interface, and one or more processors. The portable electronic device may display what appears to be a window into the imaging target (e.g., a human body), and/or an exploded view (e.g., 3-dimensional, upwardly projected image) of the target. The generated image may be a real-time continuous image of the internal features of the target (e.g., a human body) that is updated to track movements of the target (e.g., breathing patterns) and the relative position of the portable electronic device as the portable electronic device moves relative to a surface of the target.

18 Claims, 9 Drawing Sheets

(51) Int. Cl.
*A61B 8/08* (2006.01)
*G01S 15/89* (2006.01)

(52) U.S. Cl.
CPC .......... *A61B 8/4455* (2013.01); *A61B 8/4477* (2013.01); *A61B 8/4494* (2013.01); *A61B 8/483* (2013.01); *G01S 15/899* (2013.01)

(56) References Cited

U.S. PATENT DOCUMENTS

| | | |
|---|---|---|
| 4,100,916 A | 7/1978 | King |
| 4,149,247 A | 4/1979 | Pavkovich et al. |
| 4,281,550 A | 8/1981 | Erikson |
| 4,317,369 A | 3/1982 | Johnson |
| 4,541,434 A | 9/1985 | Okado |
| 4,594,662 A | 6/1986 | Devaney |
| 4,662,222 A | 5/1987 | Johnson |
| 4,798,209 A | 1/1989 | Klingenbeck et al. |
| 5,206,165 A | 4/1993 | Pauley et al. |
| 5,206,637 A | 4/1993 | Warren |
| 5,226,422 A | 7/1993 | McKeighen et al. |
| 5,269,307 A | 12/1993 | Fife et al. |
| 5,291,893 A | 3/1994 | Slayton |
| 5,335,663 A | 8/1994 | Oakley et al. |
| 5,370,121 A | 12/1994 | Reichenberger et al. |
| 5,382,521 A | 1/1995 | Raz et al. |
| 5,409,002 A | 4/1995 | Pell |
| 5,409,010 A | 4/1995 | Beach et al. |
| 5,471,515 A | 11/1995 | Fossum et al. |
| 5,471,988 A | 12/1995 | Fujio et al. |
| 5,488,952 A | 2/1996 | Schoolman |
| 5,520,188 A | 5/1996 | Hennige et al. |
| 5,611,025 A | 3/1997 | Lorensen et al. |
| 5,619,476 A | 4/1997 | Haller et al. |
| 5,650,500 A | 7/1997 | Raz et al. |
| 5,677,491 A | 10/1997 | Ishrak et al. |
| 5,740,805 A | 4/1998 | Dolazza et al. |
| 5,769,790 A | 6/1998 | Watkins et al. |
| 5,782,769 A | 7/1998 | Hwang et al. |
| 5,817,024 A | 10/1998 | Ogle et al. |
| 5,820,564 A | 10/1998 | Slayton et al. |
| 5,823,962 A | 10/1998 | Schaetzle et al. |
| 5,834,442 A | 11/1998 | Raz et al. |
| 5,873,902 A | 2/1999 | Sanghvi et al. |
| 5,893,363 A | 4/1999 | Little et al. |
| 5,894,452 A | 4/1999 | Ladabaum et al. |
| 5,922,962 A | 7/1999 | Ishrak et al. |
| 5,982,709 A | 11/1999 | Ladabaum et al. |
| 5,990,506 A | 11/1999 | Fossum et al. |
| 6,004,832 A | 12/1999 | Haller et al. |
| 6,005,916 A | 12/1999 | Johnson et al. |
| 6,007,499 A | 12/1999 | Martin et al. |
| 6,014,897 A | 1/2000 | Mo |
| 6,036,646 A | 3/2000 | Barthe et al. |
| 6,042,556 A | 3/2000 | Beach et al. |
| 6,049,159 A | 4/2000 | Barthe et al. |
| 6,093,883 A | 7/2000 | Sanghvi et al. |
| 6,128,523 A | 10/2000 | Bechtold et al. |
| 6,135,961 A | 10/2000 | Pflugrath et al. |
| 6,153,123 A | 11/2000 | Hampden-Smith et al. |
| 6,180,029 B1 | 1/2001 | Hampden-Smith et al. |
| 6,197,218 B1 | 3/2001 | Hampden-Smith et al. |
| 6,203,498 B1 | 3/2001 | Bunce et al. |
| 6,217,530 B1 | 4/2001 | Martin et al. |
| 6,224,556 B1 | 5/2001 | Schwartz et al. |
| 6,238,346 B1 | 5/2001 | Mason |
| 6,262,946 B1 | 7/2001 | Khuri-Yakub et al. |
| D456,509 S | 4/2002 | Schultz |
| 6,364,839 B1 | 4/2002 | Little et al. |
| 6,371,918 B1 | 4/2002 | Bunce |
| 6,383,139 B1 | 5/2002 | Hwang et al. |
| 6,385,474 B1 | 5/2002 | Rather et al. |
| 6,416,475 B1 | 7/2002 | Hwang et al. |
| 6,419,633 B1 | 7/2002 | Robinson et al. |
| 6,419,648 B1 | 7/2002 | Vitek et al. |
| 6,425,867 B1 | 7/2002 | Vaezy et al. |
| D461,895 S | 8/2002 | Barnes et al. |
| 6,430,109 B1 | 8/2002 | Khuri-Yakub et al. |
| 6,432,053 B1 | 8/2002 | Fecht et al. |
| 6,432,067 B1 | 8/2002 | Martin et al. |
| 6,440,071 B1 | 8/2002 | Slayton et al. |
| 6,443,896 B1 | 9/2002 | Detmer |
| 6,443,901 B1 | 9/2002 | Fraser |
| 6,447,451 B1 | 9/2002 | Wing et al. |
| 6,450,960 B1 | 9/2002 | Rather et al. |
| 6,456,326 B2 | 9/2002 | Fossum et al. |
| 6,471,651 B1 | 10/2002 | Hwang et al. |
| 6,500,133 B2 | 12/2002 | Martin et al. |
| 6,506,154 B1 | 1/2003 | Ezion et al. |
| 6,506,171 B1 | 1/2003 | Vitek et al. |
| 6,517,487 B1 | 2/2003 | Mazess et al. |
| 6,522,142 B1 | 2/2003 | Freundlich |
| 6,540,678 B2 | 4/2003 | Rather et al. |
| 6,540,679 B2 | 4/2003 | Slayton et al. |
| 6,543,272 B1 | 4/2003 | Vitek |
| 6,549,235 B1 | 4/2003 | Fossum et al. |
| 6,552,841 B1 | 4/2003 | Lasser et al. |
| 6,555,842 B1 | 4/2003 | Fossum et al. |
| 6,559,644 B2 | 5/2003 | Froundlich et al. |
| 6,569,101 B2 | 5/2003 | Quistgaard et al. |
| 6,570,617 B2 | 5/2003 | Fossum et al. |
| 6,575,908 B2 | 6/2003 | Barnes et al. |
| 6,585,731 B1 | 7/2003 | Rattner et al. |
| 6,587,540 B1 | 7/2003 | Johnson et al. |
| 6,600,325 B2 | 7/2003 | Coates et al. |
| 6,604,630 B1 | 8/2003 | Cabatic et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,632,178 B1 | 10/2003 | Fraser |
| 6,636,584 B2 | 10/2003 | Johnson et al. |
| 6,645,145 B1 | 11/2003 | Dreschel et al. |
| 6,645,162 B2 | 11/2003 | Friedman et al. |
| 6,645,398 B1 | 11/2003 | Hampden-Smith et al. |
| 6,648,826 B2 | 11/2003 | Little et al. |
| 6,659,954 B2 | 12/2003 | Robinson |
| 6,666,833 B1 | 12/2003 | Friedman et al. |
| 6,666,835 B2 | 12/2003 | Martin et al. |
| 6,669,641 B2 | 12/2003 | Poland et al. |
| 6,672,165 B2 | 1/2004 | Rather et al. |
| 6,685,639 B1 | 2/2004 | Wang et al. |
| 6,685,640 B1 | 2/2004 | Fry et al. |
| 6,694,817 B2 | 2/2004 | Degertekin et al. |
| 6,705,994 B2 | 3/2004 | Vortman et al. |
| 6,709,394 B2 | 3/2004 | Frisa et al. |
| 6,716,168 B2 | 4/2004 | Nock et al. |
| 6,716,184 B2 | 4/2004 | Vaezy et al. |
| 6,728,567 B2 | 4/2004 | Rather et al. |
| 6,734,847 B1 | 5/2004 | Baldeweg et al. |
| 6,735,461 B2 | 5/2004 | Vitek et al. |
| 6,744,068 B2 | 6/2004 | Fossum et al. |
| 6,755,786 B2 | 6/2004 | Frisa et al. |
| 6,755,788 B2 | 6/2004 | Demers et al. |
| 6,761,689 B2 | 7/2004 | Salgo et al. |
| 6,778,848 B1 | 8/2004 | Bechtold et al. |
| 6,783,497 B2 | 8/2004 | Grenon et al. |
| 6,790,180 B2 | 9/2004 | Vitek |
| 6,795,374 B2 | 9/2004 | Barnes et al. |
| 6,831,294 B1 | 12/2004 | Nishimura et al. |
| 6,831,394 B2 | 12/2004 | Baumgartner et al. |
| 6,835,177 B2 | 12/2004 | Fritz et al. |
| 6,835,393 B2 | 12/2004 | Hoffman et al. |
| 6,836,020 B2 | 12/2004 | Cheng et al. |
| 6,837,854 B2 | 1/2005 | Moore et al. |
| 6,853,357 B2 | 2/2005 | Inoue et al. |
| 6,865,140 B2 | 3/2005 | Thomenius et al. |
| 6,875,176 B2 | 4/2005 | Mourad et al. |
| 6,880,137 B1 | 4/2005 | Burlison et al. |
| 6,926,672 B2 | 8/2005 | Moore et al. |
| 6,958,255 B2 | 10/2005 | Khuri-Yakub et al. |
| 6,962,566 B2 | 11/2005 | Quistgaard et al. |
| 6,974,417 B2 | 12/2005 | Lockwood et al. |
| 6,984,210 B2 | 1/2006 | Chambers et al. |
| 7,022,077 B2 | 4/2006 | Mourad et al. |

(56) References Cited

U.S. PATENT DOCUMENTS

| | | |
|---|---|---|
| 7,030,536 B2 | 4/2006 | Smith et al. |
| 7,037,264 B2 | 5/2006 | Poland |
| 7,037,746 B1 | 5/2006 | Smith et al. |
| 7,052,464 B2 | 5/2006 | Wodnicki |
| 7,070,565 B2 | 7/2006 | Vaezy et al. |
| 7,125,383 B2 | 10/2006 | Hoctor et al. |
| 7,128,711 B2 | 10/2006 | Medan et al. |
| 7,175,596 B2 | 2/2007 | Vitek et al. |
| 7,229,411 B2 | 6/2007 | Slayton et al. |
| 7,257,051 B2 | 8/2007 | Thomenius et al. |
| 7,274,623 B2 | 9/2007 | Bayram et al. |
| 7,280,435 B2 | 10/2007 | Thomenius et al. |
| 7,285,092 B2 | 10/2007 | Duric et al. |
| 7,285,897 B2 | 10/2007 | Fisher et al. |
| 7,293,462 B2 | 11/2007 | Lee et al. |
| 7,296,318 B2 | 11/2007 | Mourad et al. |
| D558,351 S | 12/2007 | Diener et al. |
| 7,303,530 B2 | 12/2007 | Barnes et al. |
| 7,313,053 B2 | 12/2007 | Wodnicki |
| 7,321,181 B2 | 1/2008 | Khuri-Yakub et al. |
| 7,353,056 B2 | 4/2008 | Hazard et al. |
| 7,374,778 B2 | 5/2008 | Hoffman et al. |
| 7,375,420 B2 | 5/2008 | Fisher et al. |
| 7,377,900 B2 | 5/2008 | Vitek et al. |
| 7,393,325 B2 | 7/2008 | Barthe et al. |
| 7,408,283 B2 | 8/2008 | Smith et al. |
| 7,425,199 B2 | 9/2008 | Hoctor et al. |
| 7,441,321 B2 | 10/2008 | Baumgartner et al. |
| 7,441,447 B2 | 10/2008 | Degertekin et al. |
| 7,443,765 B2 | 10/2008 | Thomenius et al. |
| 7,449,640 B2 | 11/2008 | Coleman |
| 7,451,651 B2 | 11/2008 | Woychik et al. |
| 7,463,030 B2 | 12/2008 | He et al. |
| 7,470,232 B2 | 12/2008 | Hoctor et al. |
| 7,476,411 B1 | 1/2009 | Hampden-Smith et al. |
| 7,491,171 B2 | 2/2009 | Barthe et al. |
| 7,499,745 B2 | 3/2009 | Littrup et al. |
| 7,510,536 B2 | 3/2009 | Foley et al. |
| D591,423 S | 4/2009 | Diener et al. |
| 7,520,856 B2 | 4/2009 | Vaezy et al. |
| 7,521,930 B2 | 4/2009 | Li et al. |
| 7,530,356 B2 | 5/2009 | Slayton et al. |
| 7,530,952 B2 | 5/2009 | Huang et al. |
| 7,530,958 B2 | 5/2009 | Slayton et al. |
| 7,534,211 B2 | 5/2009 | Hwang et al. |
| 7,535,794 B2 | 5/2009 | Prus et al. |
| 7,545,012 B2 | 6/2009 | Smith et al. |
| 7,545,075 B2 | 6/2009 | Huang et al. |
| 7,546,769 B2 | 6/2009 | Ramaswamy et al. |
| 7,549,961 B1 | 6/2009 | Hwang |
| 7,549,962 B2 | 6/2009 | Dreschel et al. |
| 7,559,905 B2 | 7/2009 | Kagosaki et al. |
| 7,564,172 B1 | 7/2009 | Huang |
| 7,570,742 B2 | 8/2009 | Johnson et al. |
| 7,571,336 B2 | 8/2009 | Barthe et al. |
| 7,591,996 B2 | 9/2009 | Hwang et al. |
| 7,604,596 B2 | 10/2009 | Hwang et al. |
| 7,611,462 B2 | 11/2009 | Vortman et al. |
| 7,612,483 B2 | 11/2009 | Degertekin |
| 7,612,635 B2 | 11/2009 | Huang |
| 7,615,834 B2 | 11/2009 | Khuri-Yakub et al. |
| 7,621,873 B2 | 11/2009 | Owen et al. |
| 7,622,848 B2 | 11/2009 | Lee et al. |
| 7,646,133 B2 | 1/2010 | Degertekin |
| 7,652,410 B2 | 1/2010 | Prus |
| 7,662,114 B2 | 2/2010 | Seip et al. |
| 7,670,291 B2 | 3/2010 | Vaezy et al. |
| 7,684,846 B2 | 3/2010 | Johnson et al. |
| 7,686,763 B2 | 3/2010 | Vaezy et al. |
| 7,686,766 B2 | 3/2010 | Quistgaard et al. |
| 7,687,976 B2 | 3/2010 | Haider et al. |
| 7,699,780 B2 | 4/2010 | Vitek et al. |
| 7,699,783 B2 | 4/2010 | Hanover et al. |
| 7,699,793 B2 | 4/2010 | Gotte et al. |
| 7,722,539 B2 | 5/2010 | Carter et al. |
| 7,740,586 B2 | 6/2010 | Hwang et al. |
| 7,741,686 B2 | 6/2010 | Khuri-Yakub et al. |
| 7,745,248 B2 | 6/2010 | Park et al. |
| 7,745,973 B2 | 6/2010 | Bayram et al. |
| 7,758,524 B2 | 7/2010 | Barthe et al. |
| 7,759,839 B2 | 7/2010 | Huang |
| 7,759,937 B2 | 7/2010 | He et al. |
| 7,763,456 B2 | 7/2010 | Li et al. |
| 7,764,003 B2 | 7/2010 | Huang |
| 7,767,484 B2 | 8/2010 | Ayazi |
| 7,771,360 B2 | 8/2010 | Johnson et al. |
| 7,775,979 B2 | 8/2010 | Thomenius et al. |
| 7,779,696 B2 | 8/2010 | Huang |
| 7,792,566 B2 | 9/2010 | Roland et al. |
| 7,803,116 B2 | 9/2010 | Sikdar et al. |
| 7,809,400 B1 | 10/2010 | Hwang |
| 7,815,574 B2 | 10/2010 | Mourad et al. |
| 7,819,807 B2 | 10/2010 | Barnes et al. |
| 7,824,335 B2 | 11/2010 | Wodnicki |
| 7,824,348 B2 | 11/2010 | Barthe et al. |
| 7,825,383 B2 | 11/2010 | Vija et al. |
| 7,841,982 B2 | 11/2010 | Johnson et al. |
| 7,846,102 B2 | 12/2010 | Kupnik et al. |
| 7,850,626 B2 | 12/2010 | Vaezy et al. |
| 7,867,168 B2 | 1/2011 | Little et al. |
| 7,878,977 B2 | 2/2011 | Mo et al. |
| 7,880,565 B2 | 2/2011 | Huang |
| 7,888,709 B2 | 2/2011 | Lemmerhirt et al. |
| 7,892,176 B2 | 2/2011 | Wodnicki et al. |
| 7,898,905 B2 | 3/2011 | Wodnicki et al. |
| 7,903,830 B2 | 3/2011 | Hansen et al. |
| 7,914,458 B2 | 3/2011 | Hossack et al. |
| 7,920,731 B2 | 4/2011 | Moreau-Gobard |
| 7,952,260 B2 | 5/2011 | Haider et al. |
| 7,954,387 B1 | 6/2011 | Furlong |
| 7,955,264 B2 | 6/2011 | Mathew et al. |
| 7,956,510 B2 | 6/2011 | Huang |
| 7,972,271 B2 | 7/2011 | Johnson et al. |
| 7,978,461 B2 | 7/2011 | Diener et al. |
| 7,996,688 B2 | 8/2011 | Little |
| 8,002,706 B2 | 8/2011 | Vortman et al. |
| 8,003,129 B2 | 8/2011 | Hoffman et al. |
| 8,004,373 B2 | 8/2011 | Huang |
| 8,008,105 B2 | 8/2011 | Huang |
| 8,008,835 B2 | 8/2011 | Degertekin |
| 8,014,231 B2 | 9/2011 | Oliver et al. |
| 8,016,757 B2 | 9/2011 | Kaczkowski et al. |
| 8,018,301 B2 | 9/2011 | Huang |
| 8,038,620 B2 | 10/2011 | Lee et al. |
| 8,040,756 B2 | 10/2011 | Wang et al. |
| 8,052,604 B2 | 11/2011 | Lau et al. |
| 8,052,606 B2 | 11/2011 | Barnes et al. |
| 8,057,391 B2 | 11/2011 | Lau et al. |
| 8,057,409 B2 | 11/2011 | Fu et al. |
| 8,060,182 B2 | 11/2011 | He et al. |
| 8,066,642 B1 | 11/2011 | Little et al. |
| 8,076,821 B2 | 12/2011 | Degertekin |
| 8,081,301 B2 | 12/2011 | Stann et al. |
| 8,088,067 B2 | 1/2012 | Vortman et al. |
| 8,105,941 B2 | 1/2012 | Huang |
| 8,116,509 B2 | 2/2012 | Wang et al. |
| 8,116,843 B2 | 2/2012 | Dai et al. |
| 8,120,229 B2 | 2/2012 | Huang |
| 8,128,050 B1 | 3/2012 | Sliger |
| 8,131,341 B2 | 3/2012 | Heumann et al. |
| 8,133,182 B2 | 3/2012 | Wagner |
| 8,137,278 B2 | 3/2012 | Lundberg et al. |
| D657,361 S | 4/2012 | Goodwin et al. |
| 8,157,740 B2 | 4/2012 | Adachi et al. |
| 8,176,787 B2 | 5/2012 | Haider et al. |
| 8,199,685 B2 | 6/2012 | Hwang |
| 8,203,912 B2 | 6/2012 | Roest et al. |
| 8,213,467 B2 | 7/2012 | Little et al. |
| 8,216,146 B2 | 7/2012 | Hwang et al. |
| 8,222,065 B1 | 7/2012 | Smeys et al. |
| 8,226,563 B2 | 7/2012 | Petersen et al. |
| 8,231,535 B2 | 7/2012 | Hossack et al. |
| 8,237,601 B2 | 8/2012 | Dunbar et al. |
| 8,242,665 B2 | 8/2012 | Robinson et al. |

(56) References Cited

U.S. PATENT DOCUMENTS

| | | |
|---|---|---|
| 8,247,945 B2 | 8/2012 | Huang |
| 8,276,433 B2 | 10/2012 | Kupnik et al. |
| 8,277,380 B2 | 10/2012 | Daft et al. |
| 8,298,144 B2 | 10/2012 | Burcher |
| 8,309,428 B2 | 11/2012 | Lemmerhirt et al. |
| 8,315,125 B2 | 11/2012 | Lemmerhirt |
| 8,324,006 B1 | 12/2012 | Adler et al. |
| 8,327,521 B2 | 12/2012 | Dirksen et al. |
| 8,345,508 B2 | 1/2013 | Wodnicki et al. |
| 8,345,512 B2 | 1/2013 | Adachi et al. |
| 8,345,513 B2 | 1/2013 | Huang |
| 8,355,554 B2 | 1/2013 | Ma et al. |
| 8,363,514 B2 | 1/2013 | Huang |
| 8,372,011 B2 | 2/2013 | Degertekin |
| 8,388,544 B2 | 3/2013 | Hoctor et al. |
| 8,398,408 B1 | 3/2013 | Hansen et al. |
| 8,398,554 B2 | 3/2013 | Degertekin |
| 8,399,278 B2 | 3/2013 | Lemmerhirt et al. |
| 8,402,831 B2 | 3/2013 | Kupnik et al. |
| 8,409,095 B1 | 4/2013 | Marquis |
| 8,429,808 B2 | 4/2013 | Huang |
| 8,439,840 B1 | 5/2013 | Duffy |
| 8,451,693 B2 | 5/2013 | Nikoozadeh et al. |
| 8,461,978 B2 | 6/2013 | Garner et al. |
| 8,483,014 B2 | 7/2013 | Huang |
| 8,526,271 B2 | 9/2013 | Huang |
| 8,527,033 B1 | 9/2013 | Williams et al. |
| 8,551,000 B2 * | 10/2013 | Chiang ............. A61B 8/4483 600/437 |
| 8,559,274 B2 | 10/2013 | Huang |
| 8,563,345 B2 | 10/2013 | Adler et al. |
| 8,647,279 B2 | 2/2014 | Daft et al. |
| 8,658,453 B2 | 2/2014 | Lemmerhirt et al. |
| 8,672,850 B1 | 3/2014 | Miller |
| 8,689,606 B2 | 4/2014 | Schellekens et al. |
| 8,804,457 B2 | 8/2014 | Franchini et al. |
| 2001/0042853 A1 | 11/2001 | Hampden-Smith et al. |
| 2001/0051774 A1 | 12/2001 | Littrup et al. |
| 2002/0065466 A1 | 5/2002 | Rather et al. |
| 2002/0082589 A1 | 6/2002 | Friedman et al. |
| 2002/0087080 A1 | 7/2002 | Slayton et al. |
| 2002/0138000 A1 | 9/2002 | Rather et al. |
| 2002/0143245 A1 | 10/2002 | Rather et al. |
| 2002/0177774 A1 | 11/2002 | Hwang et al. |
| 2002/0180438 A1 | 12/2002 | Froundlich et al. |
| 2002/0193681 A1 | 12/2002 | Vitek et al. |
| 2003/0011362 A1 | 1/2003 | Gohlsch et al. |
| 2003/0023166 A1 | 1/2003 | Frisa et al. |
| 2003/0028111 A1 | 2/2003 | Vaezy et al. |
| 2003/0036706 A1 | 2/2003 | Slayton et al. |
| 2003/0060710 A1 | 3/2003 | Salgo et al. |
| 2003/0083597 A1 | 5/2003 | Vitek et al. |
| 2003/0097067 A1 | 5/2003 | Poland et al. |
| 2003/0097071 A1 | 5/2003 | Halmann et al. |
| 2003/0105398 A1 | 6/2003 | Vitek |
| 2003/0114760 A1 | 6/2003 | Robinson |
| 2003/0139671 A1 | 7/2003 | Walston et al. |
| 2003/0168635 A1 | 9/2003 | Hampden-Smith et al. |
| 2003/0181806 A1 | 9/2003 | Medan et al. |
| 2003/0187371 A1 | 10/2003 | Vortman et al. |
| 2003/0195421 A1 | 10/2003 | Demers et al. |
| 2003/0195422 A1 | 10/2003 | Frisa et al. |
| 2003/0204141 A1 | 10/2003 | Nock et al. |
| 2003/0208124 A1 | 11/2003 | Poland |
| 2003/0230488 A1 | 12/2003 | Lee et al. |
| 2003/0233045 A1 | 12/2003 | Vaezy et al. |
| 2004/0006272 A1 | 1/2004 | Vortman et al. |
| 2004/0015079 A1 | 1/2004 | Berger et al. |
| 2004/0030227 A1 | 2/2004 | Littrup et al. |
| 2004/0080256 A1 | 4/2004 | Hampden-Smith et al. |
| 2004/0122304 A1 | 6/2004 | Duric et al. |
| 2004/0122313 A1 | 6/2004 | Moore et al. |
| 2004/0122322 A1 | 6/2004 | Moore et al. |
| 2004/0122323 A1 | 6/2004 | Vortman et al. |
| 2004/0122325 A1 | 6/2004 | Chambers et al. |
| 2004/0169474 A1 | 9/2004 | Hampden-Smith et al. |
| 2004/0195548 A1 | 10/2004 | Hampden-Smith et al. |
| 2004/0236253 A1 | 11/2004 | Vortman et al. |
| 2004/0238732 A1 | 12/2004 | State et al. |
| 2005/0038340 A1 | 2/2005 | Vaezy et al. |
| 2005/0136102 A1 | 6/2005 | Hoffman et al. |
| 2005/0171431 A1 | 8/2005 | Petersen |
| 2005/0177045 A1 | 8/2005 | Degertekin et al. |
| 2005/0200241 A1 | 9/2005 | Degertekin |
| 2005/0200242 A1 | 9/2005 | Degertekin |
| 2005/0203397 A1 | 9/2005 | Degertekin |
| 2005/0203399 A1 | 9/2005 | Vaezy et al. |
| 2005/0219694 A1 | 10/2005 | Vesely et al. |
| 2005/0240126 A1 | 10/2005 | Foley et al. |
| 2005/0240127 A1 | 10/2005 | Seip et al. |
| 2005/0256406 A1 | 11/2005 | Barthe et al. |
| 2005/0264558 A1 | 12/2005 | Vesely et al. |
| 2006/0009693 A1 | 1/2006 | Hanover et al. |
| 2006/0009696 A1 | 1/2006 | Hanover et al. |
| 2006/0039105 A1 | 2/2006 | Smith et al. |
| 2006/0052701 A1 | 3/2006 | Carter et al. |
| 2006/0058664 A1 | 3/2006 | Barthe et al. |
| 2006/0058667 A1 | 3/2006 | Lemmerhirt et al. |
| 2006/0058671 A1 | 3/2006 | Vitek et al. |
| 2006/0058678 A1 | 3/2006 | Vitek et al. |
| 2006/0058707 A1 | 3/2006 | Barthe et al. |
| 2006/0074313 A1 | 4/2006 | Slayton et al. |
| 2006/0074355 A1 | 4/2006 | Slayton et al. |
| 2006/0079868 A1 | 4/2006 | Makin et al. |
| 2006/0084859 A1 | 4/2006 | Johnson et al. |
| 2006/0084891 A1 | 4/2006 | Barthe et al. |
| 2006/0089632 A1 | 4/2006 | Barthe et al. |
| 2006/0111744 A1 | 5/2006 | Makin et al. |
| 2006/0173338 A1 * | 8/2006 | Ma ..................... A61B 8/00 600/456 |
| 2006/0184074 A1 | 8/2006 | Vaezy et al. |
| 2006/0231795 A1 | 10/2006 | Hampden-Smith et al. |
| 2006/0250391 A1 | 11/2006 | Vesely et al. |
| 2006/0257659 A1 | 11/2006 | Hampden-Smith et al. |
| 2006/0264748 A1 | 11/2006 | Vaezy et al. |
| 2006/0282691 A1 | 12/2006 | Barthe et al. |
| 2006/0287596 A1 | 12/2006 | Johnson et al. |
| 2006/0293597 A1 | 12/2006 | Johnson et al. |
| 2007/0004984 A1 | 1/2007 | Crum et al. |
| 2007/0016039 A1 | 1/2007 | Vortman et al. |
| 2007/0041961 A1 | 2/2007 | Hwang et al. |
| 2007/0066895 A1 | 3/2007 | Sikdar et al. |
| 2007/0098232 A1 | 5/2007 | Matula et al. |
| 2007/0106157 A1 | 5/2007 | Kaczkowski et al. |
| 2007/0161896 A1 | 7/2007 | Adachi et al. |
| 2007/0167781 A1 | 7/2007 | Vortman et al. |
| 2007/0167811 A1 | 7/2007 | Lemmerhirt et al. |
| 2007/0167812 A1 | 7/2007 | Lemmerhirt et al. |
| 2007/0180916 A1 | 8/2007 | Tian et al. |
| 2007/0197918 A1 | 8/2007 | Vitek et al. |
| 2007/0215964 A1 | 9/2007 | Khuri-Yakub et al. |
| 2007/0219448 A1 | 9/2007 | Seip et al. |
| 2007/0228877 A1 | 10/2007 | Huang |
| 2007/0228878 A1 | 10/2007 | Huang |
| 2007/0232913 A1 | 10/2007 | Lau et al. |
| 2007/0239011 A1 | 10/2007 | Lau et al. |
| 2007/0239019 A1 | 10/2007 | Richard et al. |
| 2007/0239020 A1 | 10/2007 | Iinuma et al. |
| 2007/0242567 A1 | 10/2007 | Daft et al. |
| 2007/0276238 A1 | 11/2007 | Sudol |
| 2007/0287918 A1 | 12/2007 | Huang |
| 2008/0030104 A1 | 2/2008 | Prus |
| 2008/0031090 A1 | 2/2008 | Prus et al. |
| 2008/0033278 A1 | 2/2008 | Assif |
| 2008/0033292 A1 | 2/2008 | Shafran |
| 2008/0045847 A1 * | 2/2008 | Farag ................. A61B 5/02055 600/500 |
| 2008/0051656 A1 | 2/2008 | Vaezy et al. |
| 2008/0071255 A1 | 3/2008 | Barthe et al. |
| 2008/0091123 A1 | 4/2008 | Fedewa et al. |
| 2008/0091124 A1 | 4/2008 | Fedewa et al. |
| 2008/0097207 A1 | 4/2008 | Cai |
| 2008/0138290 A1 | 6/2008 | Wang et al. |
| 2008/0139973 A1 | 6/2008 | Wang et al. |

(56) References Cited

U.S. PATENT DOCUMENTS

| | | |
|---|---|---|
| 2008/0183077 A1 | 7/2008 | Moreau-Gobard et al. |
| 2008/0188745 A1 | 8/2008 | Chen et al. |
| 2008/0194053 A1 | 8/2008 | Huang |
| 2008/0197751 A1 | 8/2008 | Huang |
| 2008/0203556 A1 | 8/2008 | Huang |
| 2008/0207996 A1* | 8/2008 | Tsai .................... 600/112 |
| 2008/0255452 A1 | 10/2008 | Entrekin |
| 2008/0260790 A1 | 10/2008 | Wang et al. |
| 2008/0269614 A1 | 10/2008 | Adachi et al. |
| 2008/0275330 A1 | 11/2008 | Mu et al. |
| 2008/0275344 A1 | 11/2008 | Glide-Hurst et al. |
| 2008/0281237 A1 | 11/2008 | Slayton et al. |
| 2008/0281252 A1 | 11/2008 | Wang et al. |
| 2008/0281255 A1 | 11/2008 | Slayton et al. |
| 2008/0287835 A1 | 11/2008 | Zhao et al. |
| 2008/0290756 A1 | 11/2008 | Huang |
| 2008/0294055 A1 | 11/2008 | Adachi et al. |
| 2008/0294073 A1 | 11/2008 | Barthe et al. |
| 2008/0296708 A1 | 12/2008 | Wodnicki et al. |
| 2009/0003675 A1 | 1/2009 | Moreau-Gobard |
| 2009/0018446 A1 | 1/2009 | Medan et al. |
| 2009/0036773 A1 | 2/2009 | Lau et al. |
| 2009/0048522 A1 | 2/2009 | Huang |
| 2009/0054772 A1 | 2/2009 | Lin et al. |
| 2009/0069677 A1 | 3/2009 | Chen et al. |
| 2009/0069686 A1 | 3/2009 | Daft et al. |
| 2009/0088623 A1 | 4/2009 | Vortman et al. |
| 2009/0088636 A1 | 4/2009 | Lau et al. |
| 2009/0118725 A1 | 5/2009 | Auth et al. |
| 2009/0118729 A1 | 5/2009 | Auth et al. |
| 2009/0134497 A1 | 5/2009 | Barth et al. |
| 2009/0140606 A1 | 6/2009 | Huang |
| 2009/0140609 A1 | 6/2009 | Huang |
| 2009/0141592 A1 | 6/2009 | Huang |
| 2009/0142872 A1 | 6/2009 | Park et al. |
| 2009/0152980 A1 | 6/2009 | Huang |
| 2009/0250729 A1 | 10/2009 | Lemmerhirt et al. |
| 2009/0251917 A1 | 10/2009 | Wollner et al. |
| 2009/0259129 A1 | 10/2009 | Wang et al. |
| 2009/0280441 A1 | 11/2009 | Nara |
| 2009/0316151 A1 | 12/2009 | Matula et al. |
| 2010/0013574 A1 | 1/2010 | Huang |
| 2010/0018315 A1 | 1/2010 | Wang et al. |
| 2010/0022882 A1 | 1/2010 | Duckworth et al. |
| 2010/0036291 A1 | 2/2010 | Darlington et al. |
| 2010/0036292 A1 | 2/2010 | Darlington et al. |
| 2010/0056925 A1 | 3/2010 | Zhang et al. |
| 2010/0063397 A1 | 3/2010 | Wagner |
| 2010/0076351 A1 | 3/2010 | Jiang et al. |
| 2010/0081893 A1 | 4/2010 | Jarvik et al. |
| 2010/0087728 A1 | 4/2010 | Jarvik et al. |
| 2010/0106019 A1 | 4/2010 | Friemel et al. |
| 2010/0152587 A1 | 6/2010 | Haider et al. |
| 2010/0160781 A1 | 6/2010 | Carter et al. |
| 2010/0173437 A1 | 7/2010 | Wygant et al. |
| 2010/0174188 A1 | 7/2010 | Wang et al. |
| 2010/0191894 A1 | 7/2010 | Bartley et al. |
| 2010/0207489 A1 | 8/2010 | Huang |
| 2010/0210976 A1 | 8/2010 | Darlington et al. |
| 2010/0225200 A1 | 9/2010 | Kupnik et al. |
| 2010/0228126 A1 | 9/2010 | Emery et al. |
| 2010/0234728 A1 | 9/2010 | Foley et al. |
| 2010/0234773 A1 | 9/2010 | Fu et al. |
| 2010/0236330 A1 | 9/2010 | Nyholt et al. |
| 2010/0237807 A1 | 9/2010 | Lemmerhirt |
| 2010/0241005 A1 | 9/2010 | Darlington et al. |
| 2010/0241036 A1 | 9/2010 | Vortman et al. |
| 2010/0244623 A1 | 9/2010 | Huang |
| 2010/0246332 A1 | 9/2010 | Huang |
| 2010/0249605 A1 | 9/2010 | Degertekin |
| 2010/0251537 A1 | 10/2010 | Huang |
| 2010/0254222 A1 | 10/2010 | Huang |
| 2010/0255623 A1 | 10/2010 | Huang |
| 2010/0256488 A1 | 10/2010 | Kim et al. |
| 2010/0256501 A1 | 10/2010 | Degertekin |
| 2010/0262070 A1 | 10/2010 | Wang |
| 2010/0268089 A1 | 10/2010 | Degertekin |
| 2010/0278015 A1 | 11/2010 | Huang |
| 2010/0280388 A1 | 11/2010 | Huang |
| 2010/0298711 A1 | 11/2010 | Pedersen et al. |
| 2010/0307486 A1 | 12/2010 | Chen et al. |
| 2010/0315272 A1 | 12/2010 | Steele et al. |
| 2010/0317971 A1 | 12/2010 | Fan et al. |
| 2010/0317972 A1 | 12/2010 | Baumgartner et al. |
| 2010/0330545 A1 | 12/2010 | Tian et al. |
| 2011/0009734 A1 | 1/2011 | Foley et al. |
| 2011/0040171 A1 | 2/2011 | Foley et al. |
| 2011/0040189 A1 | 2/2011 | Petruzzello et al. |
| 2011/0040214 A1 | 2/2011 | Foley et al. |
| 2011/0050033 A1 | 3/2011 | Nikoozadeh et al. |
| 2011/0060221 A1 | 3/2011 | Fan et al. |
| 2011/0071397 A1 | 3/2011 | Wodnicki et al. |
| 2011/0084570 A1 | 4/2011 | Soeda et al. |
| 2011/0107270 A1 | 5/2011 | Wang et al. |
| 2011/0109309 A1 | 5/2011 | Levy et al. |
| 2011/0136284 A1 | 6/2011 | Huang |
| 2011/0150758 A1 | 6/2011 | Geppert et al. |
| 2011/0151608 A1 | 6/2011 | Lemmerhirt et al. |
| 2011/0178407 A1 | 7/2011 | Lu et al. |
| 2011/0178444 A1 | 7/2011 | Slayton et al. |
| 2011/0187706 A1 | 8/2011 | Vesely et al. |
| 2011/0201928 A1 | 8/2011 | Duric et al. |
| 2011/0201929 A1 | 8/2011 | Vaezy et al. |
| 2011/0201932 A1 | 8/2011 | Duric et al. |
| 2011/0201976 A1 | 8/2011 | Sanghvi et al. |
| 2011/0218436 A1 | 9/2011 | Dewey et al. |
| 2011/0242932 A1 | 10/2011 | Lebental et al. |
| 2011/0245670 A1 | 10/2011 | Tashiro et al. |
| 2011/0251528 A1 | 10/2011 | Canney et al. |
| 2011/0263997 A1* | 10/2011 | Corn .................... A61B 5/08 600/529 |
| 2011/0272693 A1 | 11/2011 | Kobayashi et al. |
| 2011/0288238 A1 | 11/2011 | Hoffman et al. |
| 2011/0313278 A1 | 12/2011 | Kiraly |
| 2011/0319736 A1* | 12/2011 | Hill .................... A61B 5/4519 600/365 |
| 2012/0005624 A1 | 1/2012 | Vesely |
| 2012/0010538 A1 | 1/2012 | Dirksen |
| 2012/0013218 A1 | 1/2012 | Huang |
| 2012/0022379 A1 | 1/2012 | Gubbini et al. |
| 2012/0029353 A1 | 2/2012 | Slayton et al. |
| 2012/0035473 A1 | 2/2012 | Sanghvi et al. |
| 2012/0046592 A1 | 2/2012 | Albright et al. |
| 2012/0071759 A1 | 3/2012 | Hagy et al. |
| 2012/0074509 A1 | 3/2012 | Berg et al. |
| 2012/0086087 A1 | 4/2012 | Fitzpatrick |
| 2012/0112324 A1 | 5/2012 | Huang |
| 2012/0162204 A1 | 6/2012 | Vesely et al. |
| 2012/0162368 A1* | 6/2012 | Choi .................... 348/45 |
| 2012/0187508 A1 | 7/2012 | Adler et al. |
| 2012/0250454 A1 | 10/2012 | Rohling et al. |
| 2012/0289829 A1 | 11/2012 | Barnes et al. |
| 2012/0299439 A1 | 11/2012 | Huang |
| 2012/0300036 A1 | 11/2012 | Flynn |
| 2013/0050422 A1 | 2/2013 | Flynn |
| 2013/0064043 A1 | 3/2013 | Degertekin et al. |
| 2013/0116561 A1 | 5/2013 | Rothberg et al. |
| 2013/0278631 A1 | 10/2013 | Border et al. |
| 2013/0314260 A1 | 11/2013 | Gemmeke et al. |
| 2014/0066763 A2 | 3/2014 | Rothberg et al. |
| 2014/0180088 A1 | 6/2014 | Rothberg et al. |
| 2014/0180092 A1 | 6/2014 | Rothberg et al. |
| 2014/0180093 A1 | 6/2014 | Rothberg et al. |
| 2014/0180094 A1 | 6/2014 | Rothberg et al. |
| 2014/0180095 A1 | 6/2014 | Rothberg et al. |
| 2014/0180096 A1 | 6/2014 | Rothberg et al. |
| 2014/0180097 A1 | 6/2014 | Rothberg et al. |
| 2014/0180099 A1 | 6/2014 | Rothberg et al. |
| 2014/0180100 A1 | 6/2014 | Rothberg et al. |
| 2014/0180112 A1 | 6/2014 | Rothberg et al. |
| 2014/0180113 A1 | 6/2014 | Rothberg et al. |
| 2014/0180176 A1 | 6/2014 | Rothberg et al. |
| 2014/0180177 A1 | 6/2014 | Rothberg et al. |
| 2014/0217478 A1 | 8/2014 | Rothberg et al. |

(56) References Cited

U.S. PATENT DOCUMENTS

| | | |
|---|---|---|
| 2014/0219062 A1 | 8/2014 | Rothberg et al. |
| 2014/0264660 A1 | 9/2014 | Rothberg et al. |
| 2014/0288428 A1 | 9/2014 | Rothberg et al. |
| 2015/0032002 A1 | 1/2015 | Rothberg et al. |
| 2015/0080724 A1 | 3/2015 | Rothberg et al. |
| 2015/0087977 A1 | 3/2015 | Rothberg et al. |

FOREIGN PATENT DOCUMENTS

| | | |
|---|---|---|
| CN | 102 981 156 A | 3/2013 |
| EP | 0 031 614 A1 | 7/1981 |
| EP | 0 985 007 A1 | 3/2000 |
| WO | WO-98/37165 A1 | 8/1998 |
| WO | WO-99/47046 A1 | 9/1999 |
| WO | WO-00/12649 A1 | 3/2000 |
| WO | WO-03/096883 A2 | 11/2003 |
| WO | WO-2004/061575 A2 | 7/2004 |
| WO | WO-2007/095499 A2 | 8/2007 |
| WO | WO-2007/096636 A1 | 8/2007 |
| WO | WO-2009135255 A1 | 11/2009 |
| WO | WO-2011/094585 A1 | 8/2011 |
| WO | WO-2011/100691 A1 | 8/2011 |
| WO | WO-2011/100697 A1 | 8/2011 |
| WO | WO-2011/156624 A2 | 12/2011 |
| WO | WO-2012/017978 A2 | 2/2012 |
| WO | WO-2014/151362 A2 | 9/2014 |

OTHER PUBLICATIONS

Ajdler et al., Sound Field Analysis Along a Circle and its Applications to HRTFs Interpolation. J Audio Eng Soc. Mar. 2008;56(3):156-75.
Ali et al., Signal Processing Overview of Ultrasound Systems for Medical Imaging. Texas Instruments White Paper. Nov. 2008;SPRAB12:1-27.
Amini et al., Noninvasive Estimation of Tissue Temperature Via High-Resolution Spectral Analysis Techniques. IEEE Trans on Biomed Eng. Feb. 2005;52(2):221-8.
Andre et al., High-Speed Data Acquisition in a Diffraction Tomography System Employing Large-Scale Toroidal Arrays. Acoust Tom. 1997;8(1):137-47.
Arnal et al., Monitoring of Thermal Therapy Based on Shear Modulus Changes: I. Shear Wave Thermometry. IEEE Trans Ultrason Ferr Freq Control. Feb. 2011;58(2):369-78.
Arnold et al., Discrete Transparent Boundary Conditions for Wide Angle Parabolic Equations in Underwater Acoustics. J Comp Phys. 1998. 6 pages.
Bavaro et al., Element Shape Design of 2-D CMUT Arrays for Reducing Grating Lobes. IEEE Trans Ultrason Ferroelectr Freq Contr. Feb. 2008;55(2):308-18.
Bolz et al., Sparse Matrix Solver on the GPU: Conjugate Gradients and Multigrid. Acm Trans Graph. Jul. 2003;22(3):917-924.
Boufounos, Compressive Sensing for Over-the-Air Ultrasound. Mitsubishi Elec Res Lab. May 2011. http://www.merl.com. 6 pages.
Calmes et al., Highly Integrated 2-D Capacitive Micromachined Ultrasonic Transducers. 1999 IEEE Ultrason Symp. 1999;1163-6.
Candes et al., An Introduction to Compressive Sampling: A sensing/sampling paradigm that goes against the common knowledge in data acquisition. IEEE Signal Proc Mag. Mar. 2008;21-30.
Candes et al., Decoding by Linear Programming. IEEE Trans Info Theory. Dec. 2005;51(12):4203-15.
Candes et al., Near-Optimal Signal Recovery From Random Projections: Universal Encoding Strategies? IEEE Trans Info Theory. Dec. 2006;52(12):5406-25.
Candes et al., Robust Uncertainty Principles: Exact Signal Reconstruction From Highly Incomplete Frequency Information. IEEE Trans Info Theory. Feb. 2006;52(2):489-509.
Candes et al., Sparsity and incoherence in compressive sampling. Inverse Problems. 2007;23:969-985. doi:10.1088/0266-5611/23/3/008.

Carson et al., Anniversary Paper: Evolution of ultrasound physics and the role of medical physicists and the AAPM and its journal in that evolution. Med Phys. Feb. 2009;36(2):411-28.
Chen et al., Atomic decomposition by basis pursuit. SIAM Rev. Mar. 2001;43(1):129-159.
Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.
Cheng et al., A 3D Parabolic Equation Method for Sound Propagation in Moving Inhomogeneous Media. Am Inst Aeronaut Astronaut Meeting Paper. 2007;3564. 20 pages.
Cheng et al., An Efficient Electrical Addressing Method Using Through-Wafer Vias for Two-Dimensional Ultrasonic Arrays. 2000 IEEE Ultrasonics Symposium. 2000;2:1179-82.
Cheng et al., CMUT-in-CMOS ultrasonic transducer arrays with on-chip electronics. Transducers 2009. IEEE. Jun. 21, 2009;1222-5.
Cheng et al., Electrical Through-Wafer Interconnects with Sub-PicoFarad Parasitic Capacitance. 2001 Microelectromechan Syst Conf. Aug. 24, 2001;18-21.
Cocosco et al., BrainWeb: Online Interface to a 3D MRI Simulated Brain Database. NeuroImage. 1997; 5:S425.
Cox, Acoustics for Ultrasound Imaging. Jan. 2012. 79 pages.
Daft et al., 5F-3 A Matrix Transducer Design with Improved Image Quality and Acquisition Rate. 2007 IEEE Ultrasonics Symposium. Oct. 1, 2007;411-5.
Daft et al., Microfabricated Ultrasonic Transducers Monolithically Integrated with High Voltage Electronics. 2004 IEEE Ultrasonics Symposium. Aug. 23, 2004;1:493-6.
Dehnavi et al., Enhancing the performance of conjugate gradient solvers on graphic processing units. IEEE Trans Magn. May 2011;47(5):1162-5.
Dehnavi et al., Enhancing the Performance of Conjugate Gradient Solvers on Graphic Processing Units. IEEE. 2010. 1 page.
Denis et al., Ultrasonic Transmission Tomography in Refracting Media: Reduction of Refraction Artifacts by Curved-Ray Techniques. IEEE Trans Med Imag. Mar. 1995;14(1):173-88.
Donoho et al., Data Compression and Harmonic Analysis. IEEE Trans Info Theory. Oct. 1998;44(6):2435-76.
Donoho et al.,Uncertainty Principles and Ideal Atomic Decomposition. IEEE Trans Info Theory. Nov. 2001;47(7):2845-62.
Donoho, Compressed Sensing. IEEE Trans Info Theory. Apr. 2006;52(4):1289-306.
Doody et al., Modeling and Characterization of CMOS-Fabricated Capacitive Micromachined Ultrasound Transducers. J Microelectromechan Sys. Feb. 2011;20(1):104-118.
Dupenloup et al., Reduction of the Grating Lobes of Annular Arrays Used in Focused Ultrasound Surgery. IEEE Trans Ultrason Ferr Freq Control. Nov. 1996;43(6):991-8.
Duric et al., Detection of breast cancer with ultrasound tomography: First results with the Computed Ultrasound Risk Evaluation (CURE) prototype. Med Phys. Feb. 2007;34(2):773-85.
Duric et al., Development of ultrasound tomography for breast imaging: Technical assessment. Med Phys. May 2005;32(5):1375-86.
Ebbini et al., Multiple-Focus Ultrasound Phased-Array Pattern Synthesis: Optimal Driving-Signal Distributions for Hyperthermia. IEEE Trans Ultrason Ferr Freq Control. Sep. 1989;36(5):540-8.
Eccardt et al., Micromachined ultrasound transducers with improved coupling factors from a CMOS compatible process. Ultrasonics. Mar. 2000;38:774-80.
Eccardt et al., Surface micromachined ultrasound transducer in CMOS technology. Proc Ultrason Symp. 1996;959-62.
Fellingham et al., Ultrasonic Characterization of Tissue Structure in the In VivoHuman Liver and Spleen. IEEE Trans Sonics Ultrason. Jul. 1984;SU-31(4):418-28.
Frigo et al., The Design and Implementation of FP 1W3. Proc IEEE. Feb. 2005;93(2):216-31.
Geller et al., Two efficient algorithms for iterative linearized inversion of seismic waveform data. Geophys J Int. 1993;115:699-710.
Ghoshal et al., Use of quantitative ultrasound to detect temperature variations in biological phantoms due to heating. IEEE Int Ultrason Symp Proc. 2009;1780-3.

(56) References Cited

OTHER PUBLICATIONS

Gurun et al., Front-end CMOS electronics for monolithic integration with CMUT arrays: circuit design and initial experimental results. Proc Ultrason Symp. 2008;390-3.

Haak et al., Comparison of spatiotemporal interpolators for 4D image reconstruction from 2D transesophageal ultrasound. Proc SPIE. Feb. 4, 2012;8320:832007.1-11.

Herman et al., High-Resolution Radar via Compressed Sensing. IEEE Trans Signal Proc. Jun. 2009;57(6):2275-84.

Hormati et al., Robust Ultrasound Travel-time Tomography Using the Bent Ray Model. Proc SPIE. 2010;7629:762901.1-12.

Huang et al., Breast imaging with time-reversed ultrasound. Proc SPIE. 2006;6147:614701.1-12.

Huang et al., In vivo breast sound-speed imaging with ultrasound tomography. Ultrasound Med Biol. 2009. 40 pages.

International Preliminary Report on Patentability mailed May 1, 2014 for Application No. PCT/US2012/060665.

International Preliminary Report on Patentability mailed on Sep. 24, 2015 for Application No. PCT/US2014/025567.

International Preliminary Report on Patentability mailed Sep. 11, 2015 for Application No. PCT/US 2014/018696.

International Search Report and Written Opinion mailed Jul. 22, 2015 for Application No. PCT/US2015/026315.

International Search Report and Written Opinion mailed Mar. 2, 2015 for Application No. PCT/US2014/047553.

International Search Report and Written Opinion mailed Nov. 4, 2014 for Application No. PCT/US2014/018696.

International Search Report and Written Opinion mailed Sep. 15, 2014 for Application No. PCT/US2014/025567.

Interview Summary mailed Apr. 6, 2015 for U.S. Appl. No. 14/561,504.

Interview Summary mailed May 7, 2015 for U.S. Appl. No. 14/561,328.

Jovanovic et al., Acoustic Tomography for Scalar and Vector Fields: Theory and Application to Temperature and Wind Estimation. Am Meteorol Soc. Aug. 2009;26:1475-92.

Jovanovic et al., Sound Speed Estimation Using Wave-based Ultrasound Tomography: Theory and GPU Implementation. Proc SPIE. 2010;7629:76290J.1-12.

Jovanovic, Inverse Problems in Acoustic Tomography: Theory and Applications. Audiovis Comm Lab EPFL. Jul. 31, 2008. 139 pages.

Kak, Computerized Tomography with X-Ray, Emission, and Ultrasound Sources. Proc IEEE. Sep. 1979;67(9)1245-72.

Kim et al., Design and Test of a Fully Controllable 64×128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

Klimes, Grid Travel-time Tracing: Second-order Method for the First Arrivals in Smooth Media. Pageoph. 1996;148(3):539-63.

Knight et al., Low Temperature Fabrication of Immersion Capacitive Micromachined Ultrasonic Transducers on Silicon and Dielectric Substrates. IEEE Trans Ultrason Ferroelectr Freq Contr. Oct. 2004;51(10): 1324-33.

Kupnik et al., CMUT Fabrication Based on a Thick Buried Oxide Layer. Proc IEEE Ultrason Symp. Oct. 2010;2010:547-550. doi:10.1109/ULTSYM.2010.5935935. Epub Jun. 8, 2012. 10 pages.

Li et al., An improved automatic time-of-flight picker for medical ultrasound tomography. Ultrason. 2009;49:61-72.

Li et al., Breast ultrasound tomography with total-variation regularization. Proc SPIE. 2009;7265:726506.1-8.

Li et al., Clinical breast imaging using sound-speed reconstructions of ultrasound tomography data. Proc SPIE. 2008;6920:692009.1-9.

Li et al., Comparison of ultrasound attenuation tomography methods for breast imaging. Proc SPIE. 2008;6920:692015.1-9.

Li et al., Refraction corrected transmission ultrasound computed tomography for application in brest imaging. Med Phys. May 2010;37(5):2233-46.

Lin et al., Packaging of Large and Low-Pitch Size 2D Ultrasonic Transducer Arrays. MEMS Conf. 2010;508-11.

Liu et al., Real-Time 2-D Temperature Imaging Using Ultrasound. IEEE Trans Biomed Eng. Jan. 2010;57(1):12-16.

Lu et al., High Frame Rate Imaging System for Limited Diffraction Array Beam Imaging with Square-Wave Aperture Weightings. IEEE Trans Ultrason Ferr Freq Control. Oct. 10, 2006;53(10):1796-812.

Lurton, An Introduction to Underwater Acoustics: Principles and Applications. 2010;13-74.

Lustig et al., Sparse MRI: The application of compressed sensing for rapid MR imaging. Magn Reson Med. Dec. 2007;58(6):1182-95.

Malcolm, Introduction to Seismic Imaging. Presentation. Mit. Aug. 20, 2010. 59 pages.

Mast, Aberration correction for time-domain ultrasound diffraction tomography. J Acoust Soc Am. Jul. 2002;112(1):55-64.

Matheney et al., Seismic attenuation values obtained from instantaneous-frequency matching and spectral ratios.Geophys J Int. 1995;123:1-15.

Misaridis, Ultrasound Imaging Using Coded Signals. Thesis submitted in partial fulfillment of the requirements for the degree of Doctor of Philosophy at the Technical University of Denmark. Aug. 2001. 228 pages.

Moros et al., An investigation of penetration depth control using parallel opposed ultrasound arrays and a scanning reflector. J Acoust Soc Am. Mar. 1997;101(3):1734-41.

Moros et al., Experimental assessment of power and tetnperature penetration depth control with a dual frequency ultrasonic system. Med Phys. May 1999;26(5):810-7.

Nikoozadeh et al., Forward-Looking Intracardiac Ultrasound Imaging Using a 1-D CMUT Array Integrated With Custom Front-End Electronics. IEEE Trans Ultrason Ferroelectr Freq Contr. Dec. 2008;55(12):2651-60.

Noble et al., A cost-effective and manufacturable route to the fabrication of high-density 2D micromachined ultrasonic transducer arrays and (CMOS) signal conditioning electronics on the same silicon substrate. Proc Ultrason Symp. 2001;941-5.

Nobel et al., Low-Temperature micromachined CMUTs with fully-integrated analogue front-end electronics. Proc Ultrason Symp. 2002;1045-50.

Novak et al., Treatment delivery software for a new clinical grade ultrasound system for thermoradiotherapy. Med Phys. Nov. 2005;32(11):3246-56.

Office Communication and Interview Summary mailed Mar. 26, 2015 for U.S. Appl. No. 14/561,328.

Office Communication mailed Mar. 16, 2015 for U.S. Appl. No. 14/561,504.

Oralkan et al., Capacitive Micromachined Ultrasonic Transducers: Next-Generation Arrays for Acoustic Imaging? IEEE Trans Ultrason Ferr Freq Control. Nov. 2002;49(11)1596-1610.

Oralkan et al., Volumetric Imaging Using 2D Capacitive Micromachined Ultrasonic Transducer Arrays (CMUTs): Initial Results. 2002 IEEE Ultrason Symp. 2002;1083-6.

Oralkan et al., Volumetric Ultrasound Imaging Using 2-D CMUT Arrays IEEE Trans Ultrason Ferroelectr Freq Contr. Nov. 2003;50(11):1581-94.

Park et al., Fabrication of Capacitive Micromachined Ultrasonic Transducers via Local Oxidation and Direct Wafer Bonding. J Microelectrotnechan Syst. Feb. 2011;20(1):95-103.

Pratt et al., Seismic waveform inversion in the frequency domain-II: Fault delineation in sediments using crosshole data. Queen's Univ. Sep. 8, 1998. Submitted to Geo[hyics Oct. 1997, revised version submitted Sep. 1998. 40 pages.

Pratt et al., Sound-speed and attenuation imaging of breast tissue using waveform tomography of transmission ultrasound data. Proc SPIE. Mar. 19, 2007;6510:651045.1-12.

Pratt, Seismic waveform inversion in the frequency domain, Part 1: Theory and verification in a physical scale model. Geophys. 1999;64(3):888-901.

Pratt, Velocity Models from Frequency-Domain Waveform Tomography: Past, Present, and Future. EAGE 66th Conf Exh. Jun. 2004. 4 pages.

Pratt, Waveform Tomography: theory and practice. Queen's Univ. 4 pages.

(56) References Cited

OTHER PUBLICATIONS

Provost et al., The application of compressed sensing for photoacoustic tomography. IEEE Trans Med Imag. Apr. 2009;28(4):585-594.
Rajagopalan et al., Variation of acoustic speed with temperature in various excised human tissues studied by ultrasound computerized tomography. Ultrason Tiss Char II. 1979; NBS Special Pub 525:227-233.
Rata et al., Endocavitary phased array applicator of therapeutic ultrasound with an integrated opposed-solenoid coil for high resolution MRI-guided thermotherapy: an in vivo study. Proc Intl Soc Mag Reson Med. 2009;17:441.
Ravaut et al., Multiscale imaging of complex structures from multifold wide-aperture seismic data by frequency-domain full-waveform tomography: application to a thrust belt. Geophys J Int. 2004;159:1032-56.
Roy et al., Robust Array Calibration using Time Delays with Application to Ultrasound Tomography. Proc SPIE. Mar. 3, 2011;7968:796806.1-11.
Saad, Iterative methods for sparse linear system, 2nd ed. Philadelphia: SIAM, 2003. Up://www.loc.govicatdirtenhancements/fy0665/2002044644-d.html Abstract only.
Sanchez, On the instrumentation of the omniscope. Thesis submitted to the Department of Electrical Engineering and Computer Science in Partial Fulfillment of the Requirements for the Degree of Master of Engineering in Electrical Engineering and Computer Science at the Massachusetts Institute of Technology. Jun. 2011. 102 pages.
Seip et al., Noninvasive estimation of tissue temperature response to heating fields using diagnostic ultrasound. IEEE Trans Biomed Eng. Aug. 1995;42(8):828-39.
Simonetti et al., Frequency Diversity in Breast Ultrasound Tomography. Proc SPIE. 2008;6913:69134E.1-8.
Singh et al., Simulation, Fabrication and Characterization of a Novel Flexible, Conformal Ultrasound Transducer Array. IEEE Ultrason Symp. Oct. 2007;1824-7.
Sirgue et al., Efficient waveform inversion and imaging: A strategy for selecting temporal frequencies. Geophys. 2004;69(1):231-48.
Taner et al., Complex seismic trace analysis. Geophys. Jun. 1979;44(6):1041-63.
Tarantola, Inversion of seismic reflection data in the acoustic approximation. Geophys. Aug. 1984;49 (8):1259-66.
Tsuji et al., Low Temperature Process for CMUT Fabrication with Wafer Bonding Technique. IEEE Intl Ultrason Symp Proc. 2010;551-4.
Um et al., An Analog-Digital-Hybrid Single-Chip RX Beamformer with Non-Uniform Sampling for 2D-CMUT Ultrasound Imaging to Achieve Wide Dynamic Range of Delay and Small Chip Area. IEEE International Solid-State Circuits Conference. Feb. 12, 2014;426-8.
Van Dongen et al., A forward model and conjugate gradient inversion technique for low-frequency ultrasonic imaging. J Acoust Soc Am. Oct. 2006;120(4):2086-95.
Van Dongen et al., A full vectorial contrast source inversion scheme for three-dimensional acoustic imaging of both compressibility and density profiles. J Acoust Soc Am. Mar. 2007;121(3):1538-49.
Wodnicki et al., Multi-Row Linear CMUT Array Using CMUTs and Multiplexing Electronics. Proc Ultrason Symp. 2009;2696-9.
Wolenenbuttel et al., Low-temperature silicon wafer-to-wafer bonding using gold at eutectic temperature. Sensors and Actuators A. 1994;43:223-9.
Wong et al., Capacitive Micromachined Ultrasonic Transducers for Therapeutic Ultrasound Applications. IEEE Trans Biomed Eng. Jan. 2010;57(1):114-23.
Wygant et al. Integration of 2D CMUT Arrays with Front-End Electronics for Volumetric Ultrasound Imaging. IEEE Trans Ultrason Ferr Freq Control. Feb. 2008;55(2):327-42.
Zahorian et al., Single chip CMUT arrays with integrated CMOS electronics: fabrication process development and experimental results. Proc Ultrason Symp. 2008;386-9.
Zhuang et al., Wafer-bonded 2-D CMUT arrays incorporating through-wafer trench-isolated interconnects with a supporting frame. IEEE Trans Ultrason Ferroelectr Freq Control. Jan. 2009;56(1):182-92. doi: 10.1109/TUFFC.2009.1018.
International Search Report for PCT/US2014/032803, mailed Nov. 13, 2014.
[No Author Listed] *HIFU Treatment Process—Step by Step.* http://www.hifu.cathifu-treatment-process-step-by=step.htm [last accessed Oct. 12, 2012]. 2 pages.
[No Author Listed], Technical Publications: Vscan Version 1.x.x CE0470 User manual GM092102. Revision 05. GE Healthcare. 2011. Chapters 1-5. 81 pages.
[No Author Listed], Universal Series Bus 3.0 Specification. Revision 1.0. Hewlett-Packard Company, Intel Corporation, Microsoft Corporation, NEC Corporation, STEricsson, and Texas Instruments. Jun. 6, 2011. 531 pages.
Ajdler et al., Sound Field Analysis Along a Circle and its Applications to HRTFs Interpolation. Audiovis Comm Lab EPFL. Jan. 30, 2008. 43 pages.
Brenders et al., Waveform Tomography of a 2-D Full Wavefield, Elastic, Wide Angle, Synthetic Dataset. Commis Contr-Sour Seismol 12th Int Worksh. Oct. 2003. 4 pages.
Kupnik et al., Wafer-Bonded CMUT Meets CMOS. 2010 CMOS Emerging Technology Workshop. May 21, 2010;1-22.

\* cited by examiner

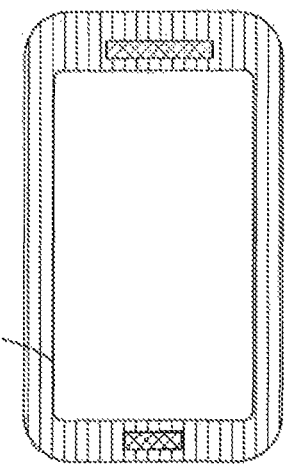
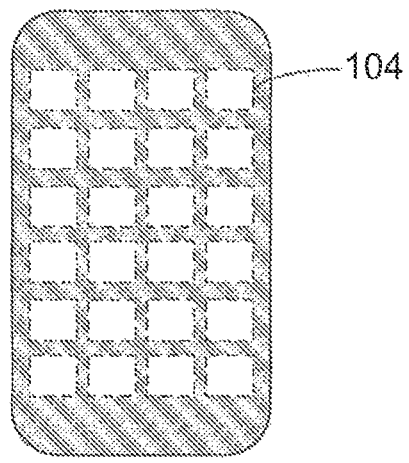
FIG. 2A  FIG. 2B
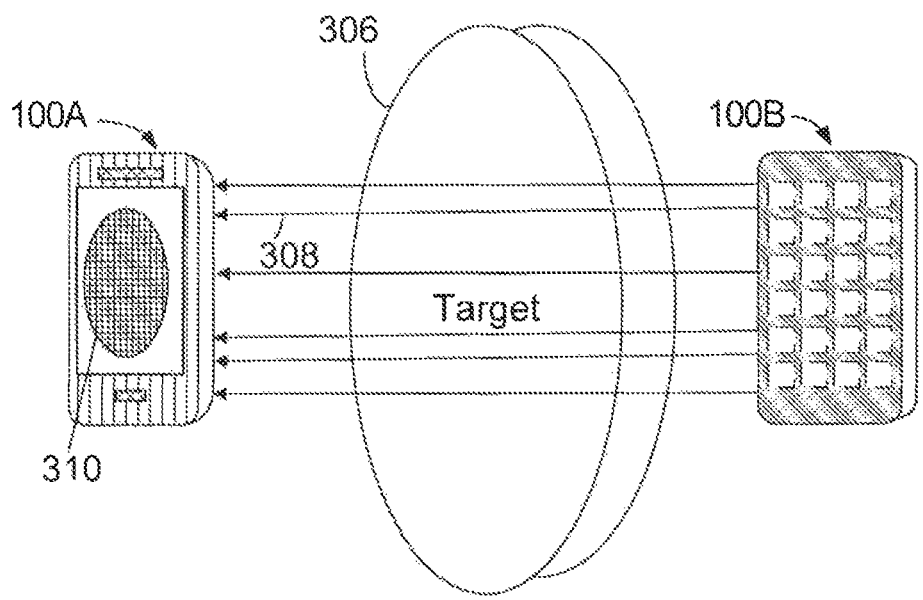
FIG. 3 to scale. Items appearing in multiple figures are
PORTABLE ELECTRONIC DEVICES WITH INTEGRATED IMAGING CAPABILITIES

FIELD OF THE TECHNOLOGY

The present disclosure relates generally to imaging devices and methods (e.g., ultrasound imaging devices and methods).

BACKGROUND

Imaging technologies are used at various stages of medical care. For example, imaging technologies are used to non-invasively diagnose patients, to monitor the performance of medical (e.g., surgical) procedures, and/or to monitor post-treatment progress or recovery.

Conventional imaging devices and methods, including magnetic resonance imaging (MRI) technology, are typically configured for and limited to use within a fixed location in a hospital setting. MRI technology is also generally slow, and suffers from other drawbacks including high cost, loud noise, and the use of potentially harmful magnetic fields.

In view of the foregoing, it would be desirable to provide portable electronic devices and associated methods with integrated imaging capabilities.

SUMMARY

Some embodiments of the present disclosure relate to a portable electronic device (e.g., smart phone and/or tablet computer) for generating and displaying an image (e.g., 2-dimensional or 3-dimensional image) of what appears to be a window into an underlying object, such as a human body, when placed in proximity to (e.g., on or close to) the object. The window and corresponding image displayed on a display screen of the portable electronic device change as the portable electronic device is moved over various portions of the body (e.g., abdomen, thorax, etc.). The image displayed by the portable electronic device may identify, for example, organs, arteries, veins, tissues, bone, and/or other bodily contents or parts. In various embodiments, the image may be presented in 3 dimensions such at it appears to the viewer as if the viewer is looking into the body, or as if the body parts have been projected up (e.g., exploded view) from the body.

The present disclosure provides numerous embodiments of systems, apparatus, computer readable media, and methods for providing imaging functionality using a portable electronic device, such as, for example, a smart phone or a tablet computer. In some embodiments, the portable electronic device is configured to generate and display an image of what appears to be an exploded view (e.g., 3-dimensional, upwardly projected image) of an object or its constituent parts. In some embodiments, movement of the portable electronic device results in the rendering of a different internal image of the target (e.g., different portion(s) of a human body). In some embodiments, the generated window of the underlying object (e.g. the portion of the human body) may provide an internal view of the object (e.g., a three-dimensional rendering of an organ or a portion of an organ).

In some embodiments according to one aspect of the present disclosure, a portable electronic device is provided that includes a processor configured to generate an image (e.g., ultrasound image) of an internal feature of a target when the device is positioned at an external surface of the target, and a display configured to display the image.

In some embodiments according to another aspect of the present disclosure, a portable ultrasound device is provided that includes multiple ultrasound elements configured to receive ultrasound radiation reflected by or passing through a target when the ultrasound device is pointed at the target. The portable ultrasound device also includes a display configured to display an image of an internal feature of the target based at least in part on the ultrasound radiation received by the plurality of ultrasound elements.

In some embodiments according to another aspect of the present disclosure, a method is provided that includes pointing a portable electronic device at an external surface of a subject, and viewing, on a display of the portable electronic device, an image of an internal feature of the subject while pointing the portable electronic device at the external surface of the subject. In some embodiments, the portable electronic device includes a radiation sensor, and the method further includes receiving, with the radiation sensor, radiation reflected by or passing through the subject, and creating the image of the internal feature based at least in part on the radiation received by the radiation sensor.

In some embodiments according to yet another aspect of the present disclosure, a portable electronic device is provided that renders within a window on a display of the device an image (e.g., 3-dimensional image) of an inside of a human body when the device is directed at the body (e.g., within about one meter or less of the body). In some embodiments, the image changes to reflect additional body parts as the device is moved relative to the body.

In some embodiments according to another aspect of the present disclosure, a portable electronic device is provided that includes multiple imaging elements configured to receive radiation signals transmitted through or reflected by an imaging target and an imaging interface. The portable electronic device also includes one or more processors configured to receive one or more sensing signals from at least one of the plurality of imaging elements, and to render an image of the imaging target for display through the imaging interface based at least in part on the one or more sensing signals.

BRIEF DESCRIPTION OF DRAWINGS

Aspects and embodiments of the present disclosure will be described with reference to the following figures. It should be appreciated that the figures are not necessarily drawn to scale. Items appearing in multiple figures are indicated by the same reference number in all the figures in which they appear.

FIG. 2A illustrates a front view of portable electronic device including an imaging interface according to some embodiments of the present disclosure.

FIG. 2B illustrates a back view of portable electronic device including imaging elements according to some embodiments of the present disclosure.

FIG. 3 illustrates a transmissive imaging system and method according to some embodiments of the present disclosure.

DETAILED DESCRIPTION

According to some embodiments of the present disclosure, a portable electronic device is provided that includes an imaging interface and one or more imaging elements. For example, the portable electronic device may be a cellular phone, personal digital assistant, smart phone, tablet device, digital camera, laptop computer, or the like. An image may be generated and/or rendered utilizing the portable electronic device. For example, the portable electronic device may be utilized to simulate as "window" into an imaging target, such as a human body or portion of the body. The simulated "window" may provide a view of the inside of a human body or portion of the body, including organs, arteries, veins, tissues, bone, and/or other bodily contents or parts. For example, an image (e.g., ultrasound or sonographic image) may be generated that illustrates and/or simulates internal features of the imaging target for a user. In some embodiments, a real-time continuous or substantially real-time continuous image may be generated and/or rendered such that movement of the portable electronic device results in a substantially real-time updated image of the area that corresponds to the new position of the portable electronic device. In some embodiments, internal movement of the target object (e.g., such as expansion and/or contraction of organs) may be rendered in real-time by the portable electronic device.

In some embodiments, the portable electronic devices and methods described herein may include, be coupled to (e.g., via a suitable communications connection or port such as a USB link), or otherwise utilize one or more radiation sources, sensors, and/or transducers (e.g., array(s) of ultrasound transducers), front-end processing circuitry and associated processing techniques, and/or image reconstruction devices and/or methods, in order to generate and/or render images to a user according to the non-limiting embodiments described in detail throughout the present disclosure.

In some embodiments of the present disclosure, one or more of the devices described in FIGS. 1A-8E herein may include or be coupled to one or more ultrasound imaging elements (e.g., one or more arrays of ultrasound sources, sensors, and/or transducers). One or more computers or processors within the portable electronic device may perform image analysis and/or image rendering based at least in part on radiation signals received by an imaging device.

Figure 1A:
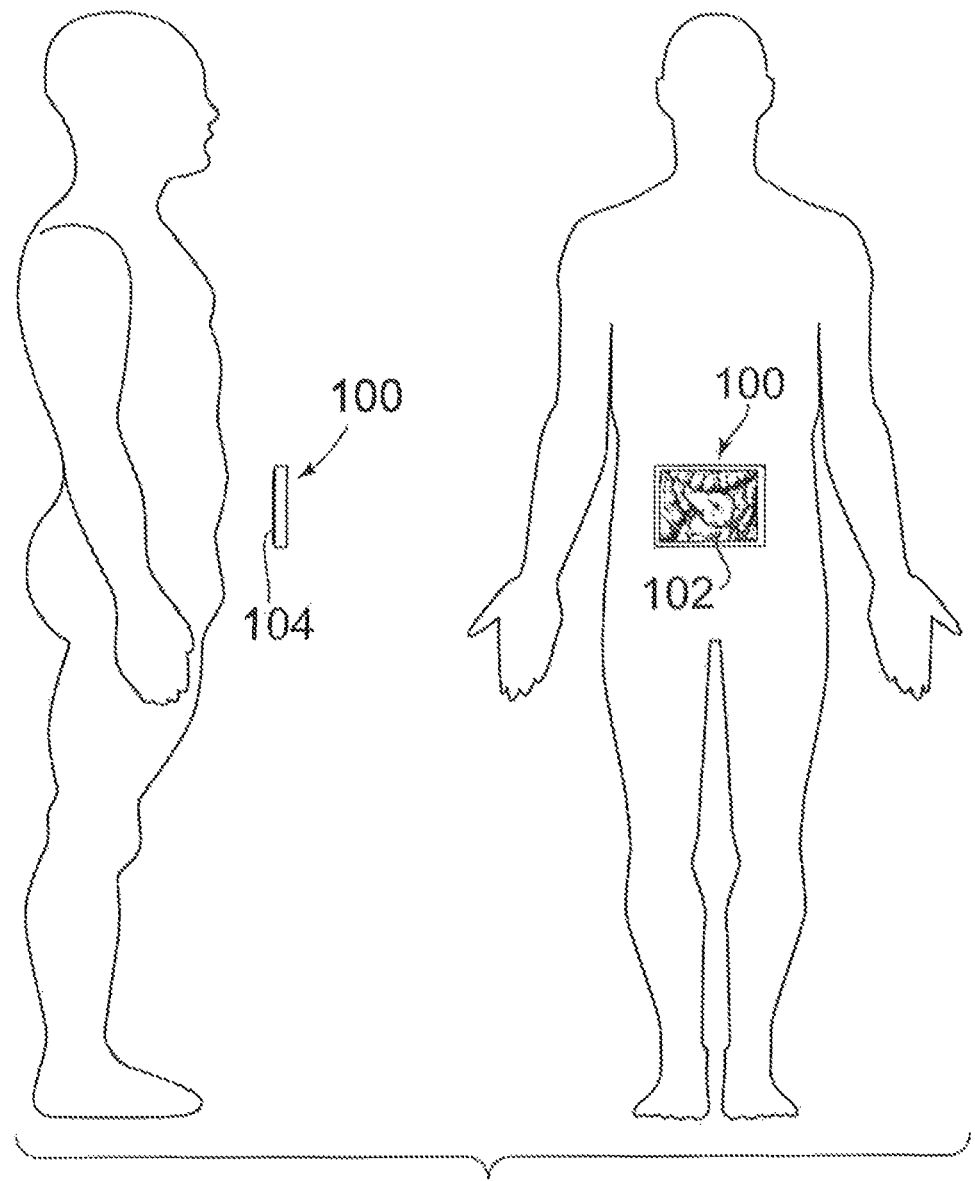
FIG. 1A illustrates a portable electronic device including an imaging interface for generating and/or rendering an internal image of a human body or a portion of a human body according to some embodiments of the present disclosure.
Figure 1B:
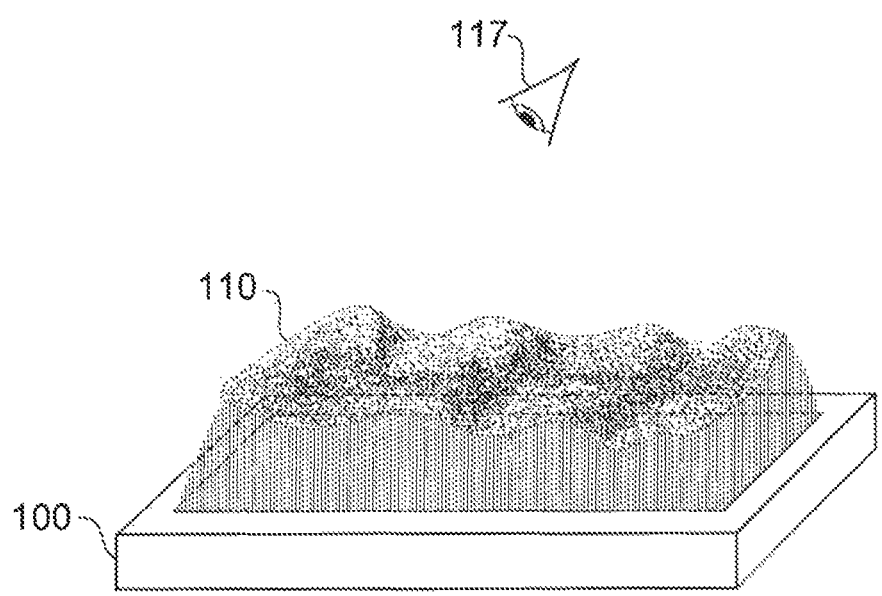
FIG. 1B illustrates a three-dimensional internal image of a portion of a human body that is generated and/or rendered by a portable electronic device according to some embodiments of the present disclosure.

FIG. 1A illustrates a portable electronic device 100 including an imaging interface 102 for generating and/or rendering an internal image of a human body or a portion of a human body 106 according to some embodiments. FIG. 1B illustrates a three-dimensional internal image 110 of a portion of a human body that is generated and/or rendered by a portable electronic device 100 according to some embodiments. As shown in. FIG. 1A, the portable electronic device 100 may be positioned in an area near (e.g., in contact with the surface of or within about one meter from the surface of) a portion of a human body that is to be imaged and/or analyzed. The portable electronic device 100 may include imaging elements 104 that are configured to transmit and/or receive radiation signals. The imaging elements 104 along with other components and functions of the portable electronic device 100 according to some embodiments of the present disclosure will be described in greater detail below with reference to FIG. 2A-2B. An internal image 110 as shown in FIG. 1B may be generated by the portable electronic device 100. The internal image 110 may be a three-dimensional internal image of a portion of the human body that appears to a viewer 117 to project upward from a surface of the portable electronic device 100, giving the viewer the perception of a viewing window into the underlying body. Through generation of the internal image, the portable electronic device 100 may provide a window into the internal areas of the human body that are below the surface. As will be described in greater detail below with reference to FIGS. 6A-6C, the generated images may be real-time continuous images such that the images are dynamically updated based on movement of the portable electronic device 100 and/or the image target (e.g., internal organs of the human body).

FIG. 2A illustrates a front view of portable electronic device 100 including an imaging interface 102 according to some embodiments of the present disclosure. The imaging interface 102 of the portable electronic device 100 may include a display that is configured to output a two-dimensional (2-D) or three-dimensional (3-D) image of an imaging target. In some embodiments, the imaging interface 102 is interactive and is capable of receiving user input, for example through a touch-screen. An image that is displayed via the imaging interface 102 may be adjusted based on the received inputs, for example, to adjust zoom level, centering position, level of detail, depth of an underlying object to be imaged, resolution, brightness, color and/or the like of the image. For example, in some embodiments, imaging interface 102 may be configured to allow a user to selectively traverse various layers and imaging depths of the underlying object using, for example, the touch screen.

Portable electronic device 100 may render a three-dimensional image of the imaging target using any suitable method or combination of methods (e.g., anaglyph, polarization, eclipse, interference filtering, and/or austosteroscopy). For example, in some embodiments, the imaging interface 102 includes a circular polarizer and/or a linear polarizer such that a viewer having polarizing filtering spectacles can view a three-dimensional image. In some embodiments, the imaging interface 102 is configured to display alternating left and right images such that a viewer having spectacles with shutters that alternate in conjunction with the displayed image. In some embodiments, the imaging interface 102 may utilize an autostereoscopy method such that 3-D spectacles are not necessary for use by a viewer to view the three-dimensional image.

In some embodiments, portable electronic device 100 may display information (e.g., text and/or graphics) in addition to (e.g., graphically overlaid on top of or adjacent to) an image of a targeted object, such as, for example, text and/or graphics identifying the structure(s) identified in the image (e.g., organs, arteries, veins, tissues, bone, and/or other bodily contents or parts). In some embodiments, portable electronic device 100 may include one or more processors for identifying structure(s) identified in the image based at least in part on stored data (e.g., data stored in random access memory or other storage device of portable electronic device 100). For example, data stored within device 100 may identify characteristic(s) of structure(s) (e.g., one or more shapes, colors, textures, cellular characteristics, tissue characteristics, and/or other distinctive and/or surrounding features or structures) that may be present within different areas of the human body for use by personal electronic device 100 to identify and/or predict the type(s) of structures depicted in an image rendered by device 100. In some embodiments, data stored within device 100 may identify characteristics of particular disease(s) such as cancer or other abnormalities for use by personal electronic device 100 to identify and/or predict the type(s) of structures depicted in an image rendered by device 100. In some embodiments, the image, text, graphics, and/or other information displayed on the user interface 104 may be adjusted through user interaction with one or more inputs (e.g., touch screen, buttons, touch-sensitive areas, or the like) of the portable electronic device 100.

FIG. 2B illustrates a back view of portable electronic device 100 including imaging elements 104 according to some embodiments of the present disclosure. The imaging elements 104 may be configured as sources (emitters) and/or sensors of ultrasound radiation and/or other radiation. In some embodiments, the imaging elements 104 may be of substantially the same size and/or may be arranged in an array as shown in FIG. 2B. In some embodiments, the imaging elements 104 may be of different sizes and/or arranged in an irregular or scattered configuration. In some embodiments, one or more (e.g., all) of the imaging elements 104 may be arranged in the same plane. In other embodiments, at least some of imaging elements may be arranged in at least two different planes. In some embodiments, all of the imaging elements 104 included in the portable electronic device 100 may be either emitting elements or sensing elements. In some embodiments, the imaging elements 104 may include both emitting elements and sensing elements. The embodiment shown in FIG. 2B includes a 4×6 array of imaging elements 104, by way of illustration only and is not intended to be limiting. In other embodiments, any other suitable numbers of imaging elements may be provided (e.g., 10, 20, 30, 40, 50, 100, 200, 500, 1000, or any number in between, or more) and may be arranged in any suitable configuration.

In some embodiments, the imaging elements 104 may be integrated within a circuit board (e.g., a printed circuit board) that includes, for example, processing (e.g., image processing) components of the portable electronic device 100. In some embodiments, the imaging elements 104 may be provided on a separate circuit board or layer of a circuit board than the processing components of the portable electronic device 100, and may be in communication with the processing circuitry through a suitable communications link (e.g., an internal bus, USB link, or other port).

The imaging elements 104 according to some embodiments of the present disclosure may include their own dedicated processing circuitry, such as a graphic processing unit (GPU), digital signal processor (DSP), and/or central processing unit (CPU), and/or may utilize processing circuitry of the portable electronic device 100. For example, in some embodiments, the CPU and/or GPU of the portable electronic device 100 may be utilized for image acquisition/ reconstruction and image rendering. In some embodiments, the CPU of portable electronic device 100 may be utilized to process computations based on received signals (e.g., backscattered signals and/or transmissive signals) in order to generate an image or topography, while the GPU may be utilized to render an image based on the information received from the CPU to generate a real-time or substantially real-time image display. In some embodiments, portable electronic device 100 may include one or more components for processing, filtering, amplification, and/or rendering images.

FIG. 3 illustrates a transmissive imaging system and method 301 according to some embodiments of the present disclosure. As shown in FIG. 3, the transmissive imaging system 301 includes two portable electronic devices 100A and 100B that are on opposing or generally opposing sides of an imaging target 306. In other embodiments, devices 100A and 100B may be positioned in any other relationship with respect to one another. In some embodiments, devices 100A and/or 100B may include one or more sensors for determining the relative positions of these devices to aid in the generation of image(s). While shown as a portable electronic device 100B (e.g., smart phone), in some embodiments device 100B may be a dedicated sensing and/or emitting device such as an array of ultrasound elements and associated circuitry. Signals (e.g., waves or beams 308) emitted from the portable electronic device 100B are sensed by the portable electronic device 100A and are utilized to render a 2-D or 3-D image 312 (e.g., real-time or substantially real-time image) of the target 306. In some embodiments, a generated 3-D image may be in the form of a pop-out image or a depth image. In some embodiments, the portable electronic device 100A may be configured to transmit signals (e.g., waves or beams) 308 though the target 306 to be received by the portable electronic device 100B. In some embodiments, the portable electronic device 100B may simultaneously or substantially simultaneously render an image (e.g., back view or alternate view or level of detail of an image rendered by device 100A) based at least in part on processing sensed signals. In some embodiments, the portable electronic devices 100A and/or 100B may communicate the results of the sensed signals to the other in order to generate or improve a rendered image.

Figure 4:
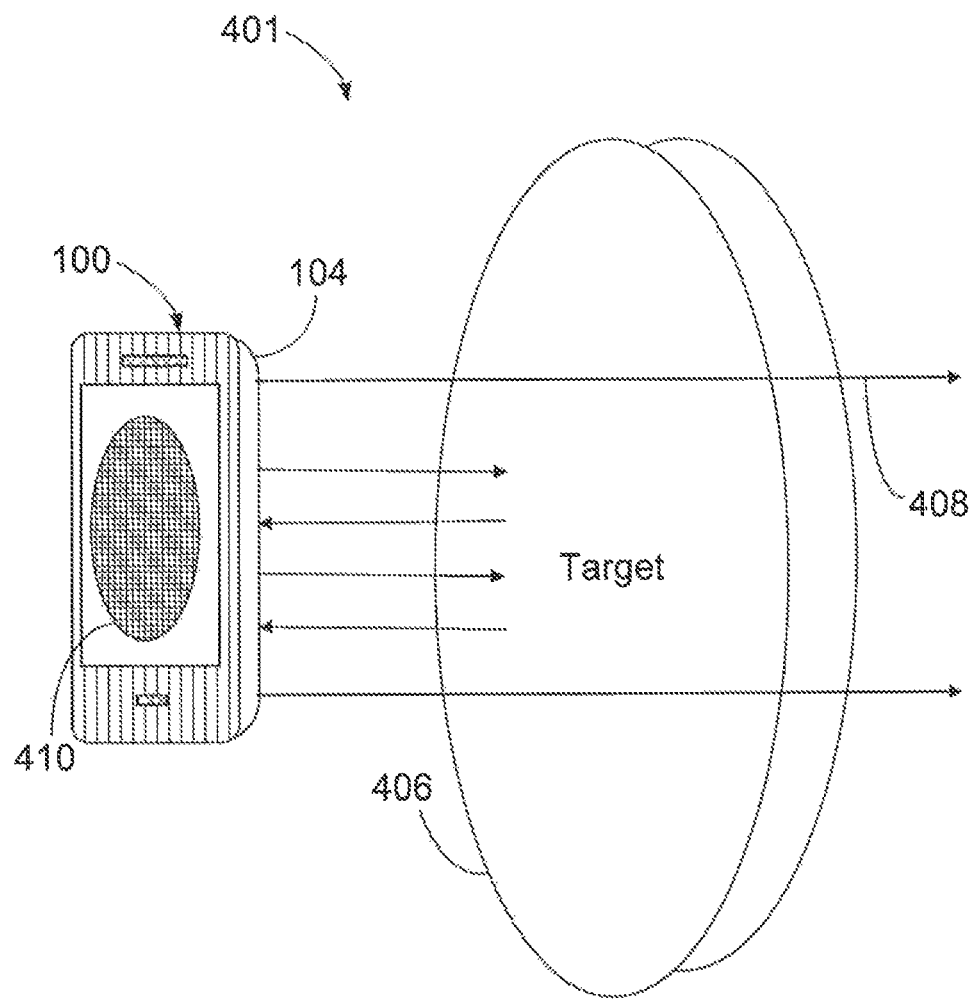
FIG. 4 illustrates a reflective imaging system and method according to some embodiments of the present disclosure.

FIG. 4 illustrates a back-scatter or reflective imaging system and method 401 according to some embodiments of the present disclosure. As shown in FIG. 4, a portable electronic device 100 may utilize emission and/or sensing elements 104 in order to render an image 410 based at least in part on reflection (e.g., back-scatter effect) of the signals 408. In some embodiments, portable electronic device 100 is the only device utilized in order to image the target (e.g., to produce an image appearing as a window into a human body). For example, the portable electronic device 100 may include both radiation sources and sensors (e.g., separate sources and sensors, and/or multiple transducers functioning as both sources and sensors), where all or substantially all of the radiation utilized by the sensors to reconstruct image(s) is backscatter radiation or radiation produced through a similar effect.

Figure 5:
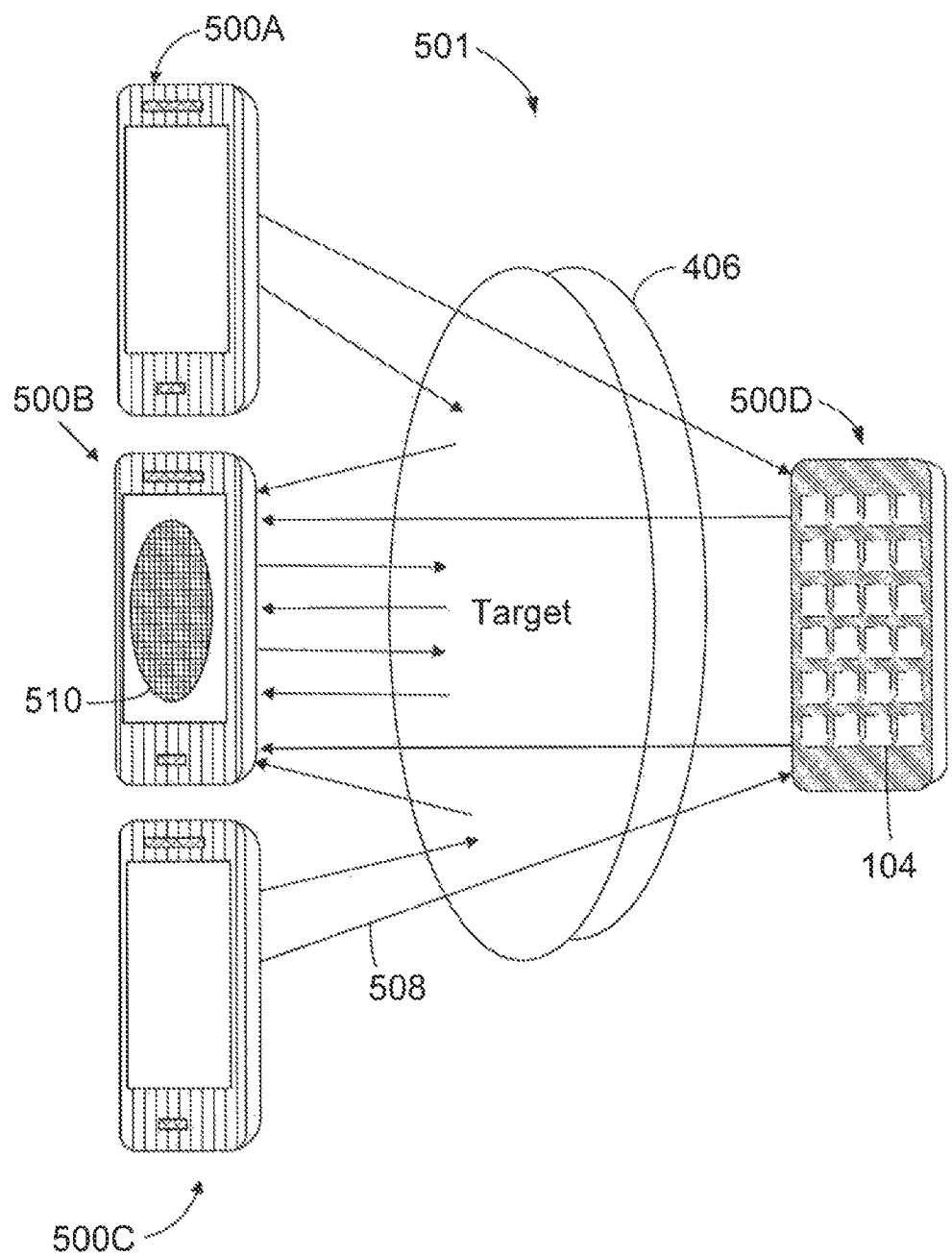
FIG. 5 illustrates a transmissive and/or reflective imaging system and method according to some embodiments of the present disclosure.

FIG. 5 illustrates a transmissive and/or reflective imaging system and method 501 according to some embodiments of the present disclosure. As shown in FIG. 5, a plurality of devices, such as portable electronic devices 500A, 500B, 500C, and/or 500D may be utilized in order to render one or more image(s) 510 of target 506 on portable electronic device 500B. Each of the portable electronic devices 500A-500D may be configured to emit signals (e.g., waves or beams) 508 as shown in FIG. 5. The image 510, or alternate views of the image or imaged structure, may be rendered on the other portable electronic devices (e.g., 500A, 500C, and 500D) through communication with one-another. In some embodiments, each of the devices (e.g., 500A, 500C, and/or 500D) may be configured as emitting and/or sensing devices only. The image 510 that is rendered on portable device 500B ma be based at least in part on signals 508 that are emitted by one or more of the devices 500A-500D, and which are sensed through reflection (e.g., back-scatter) and/or transmission by one or more of the devices 500A-500D.

In some embodiments, one or more portable electronic devices according to the present disclosure may generate and/or render an image based solely on signals received by one or more sensors (e.g., ultrasound transducers) of the device. In some embodiments, one or more portable electronic devices according to the present disclosure may generate and/or render an image based at least in part on information stored in memory (e.g., random access memory) of the portable device(s) identifying detail(s) regarding the structure(s), part(s), composition(s), and/or other characteristic(s) of object(s) to be imaged. For example, in some embodiments, when data received by one or more sensor(s) of the portable electronic devices indicates that the object being imaged is a particular body part or region, the portable electronic devices may use stored data in addition to the received data in order to generate an image of the object and/or its constituent part(s), and/or to provide addition detail or explanation regarding an object and/or its constituent parts.

Figure 6A:
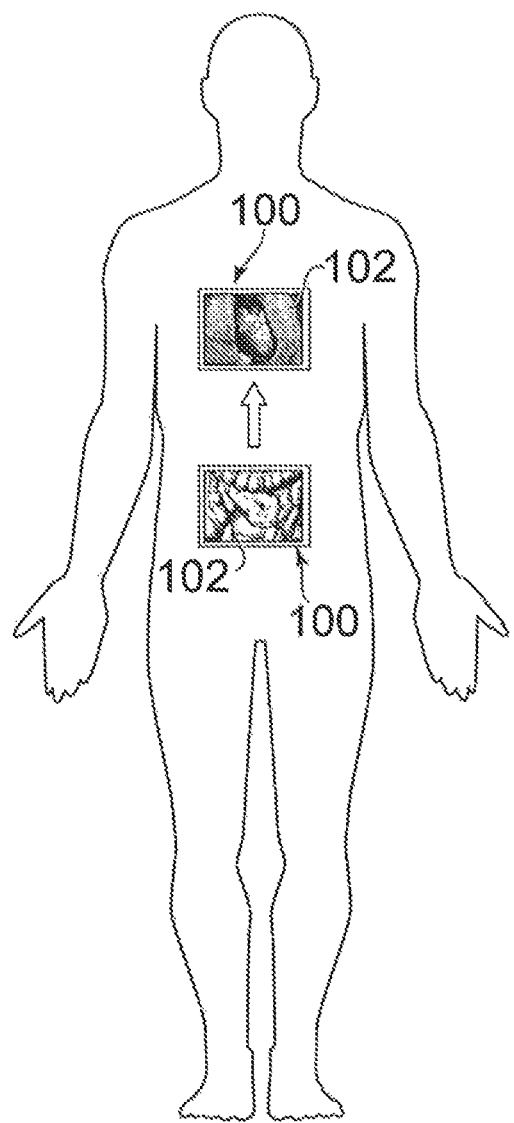
FIG. 6A illustrates a portable electronic device including an imaging interface for generating and/or rendering an internal image of a portion of a human body at a first position and at a second position according to some embodiments of the present disclosure.
Figure 6B:
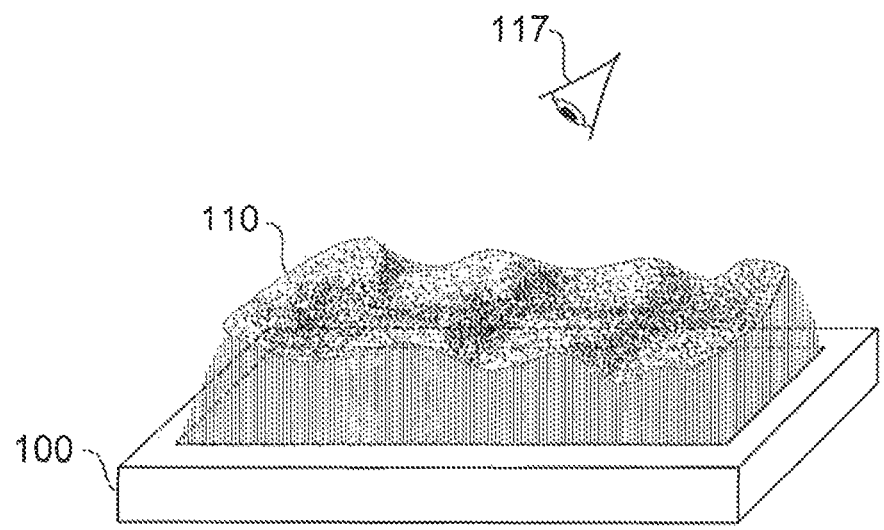
FIG. 6B illustrates a three-dimensional internal image of a portion of a human body at the first position shown in FIG. 6A that is generated and/or rendered by a portable electronic device according to some embodiments of the present disclosure.
Figure 6C:
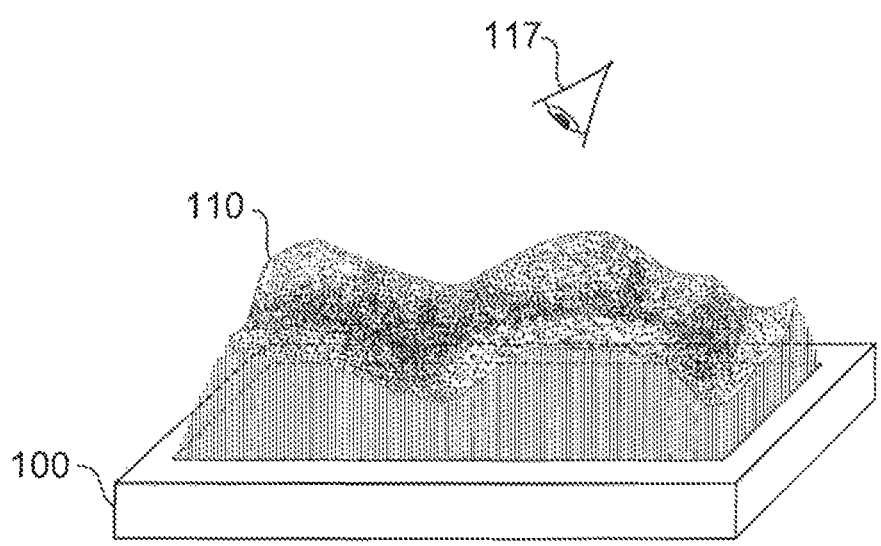
FIG. 6C illustrates a three-dimensional internal image of a portion of a human body at the second position shown in FIG. 6A that is generated and/or rendered by a portable electronic device according to some embodiments of the present disclosure.

In some embodiments of the present disclosure, the generated and/or rendered image may be a real-time or substantially real-time image that is dynamically updated based on movement of a portable electronic device 100 along a surface of an imaging target and/or motion of the imaging target. FIG. 6A illustrates a portable electronic device 100 including an imaging interface 102 for generating and/or rendering an internal image of a portion of a human body at a first position and at a second position according to some embodiments. FIG. 6B illustrates a three-dimensional internal image 610 of a portion of a human body at the first position shown in FIG. 6A that is generated and/or rendered by a portable electronic device 100 according to some embodiments. FIG. 6C illustrates a three-dimensional internal image 610 of a portion of a human body at the second position shown in FIG. 6A that is generated and/or rendered by a portable electronic device 100 according to some embodiments. As shown in FIG. 6B, a three-dimensional internal image 610 of a portion of the human body may generated and displayed to a viewer 617. The three-dimensional image 610 may appear to the viewer 617 as an image having variations in, for example, topography that correspond to the surfaces and/or other aspects or features of the internal portion of the body at the first position of the portable electronic device 100 as shown in FIG. 6A. The three-dimensional image 610 may be a real-time continuous image that is dynamically updated based on movement of the portable electronic device 100 and/or the internal portion of the body that is being analyzed. As shown in FIG. 6C, a different three-dimensional internal image 610 is displayed to the viewer 617 showing different underlying structures and/or aspects (e.g., organs, arteries, veins, tissues, bone, and/or other bodily contents or parts). The three-dimensional internal image 610 shown in FIG. 6C corresponds to the internal image of the body portion corresponding to the second position of the portable electronic device 100 as shown in FIG. 6A. As shown in FIG. 6C, the internal image 610 is illustrated as a different image showing different topographical and/or other aspects or features of the body portion than the internal image 610 shown in FIG. 6B. As discussed above, through selection of different aspect ratios and/or zoom settings, as well as through positioning of the portable electronic device 600, different types of internal images of a target may be generated, such as a three-dimensional view of an entire organ or multiple organs.

Figure 7A:
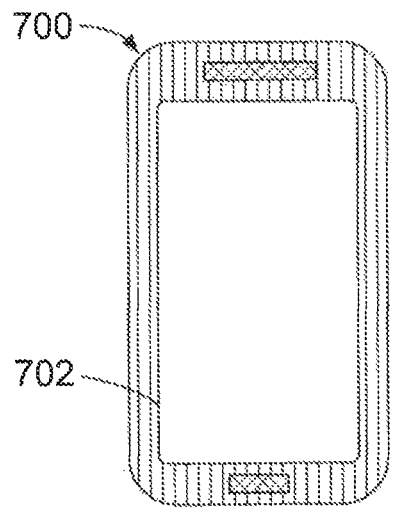
FIG. 7A illustrates a front view of a portable electronic device according to some embodiments of the present disclosure.
Figure 7B:
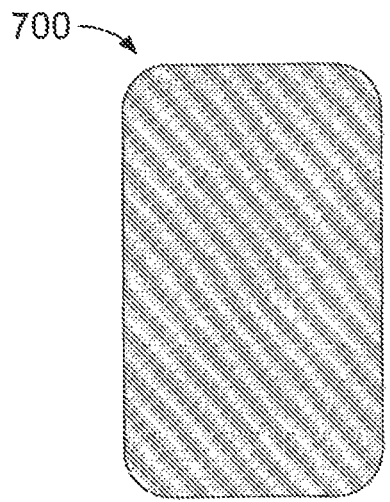
FIG. 7B illustrates a back view of a portable electronic device according to some embodiments of the present disclosure.

In some embodiments, the imaging elements, including sensors and/or sources (e.g., transducers), may be provided on, in, or otherwise coupled to a case for a portable electronic device. FIG. 7A illustrates a front view of a portable electronic device 700 according to some embodiments of the present disclosure. The portable electronic device 700 includes an imaging interface 702. FIG. 7B illustrates a back view of the portable electronic device 700 according to some embodiments of the present disclosure. As shown in FIGS. 7A and 7B, unlike the portable electronic device 100, the portable electronic device 700 does not include imaging elements 104 as part of the main housing or enclosure of device 700.

Figure 7C:
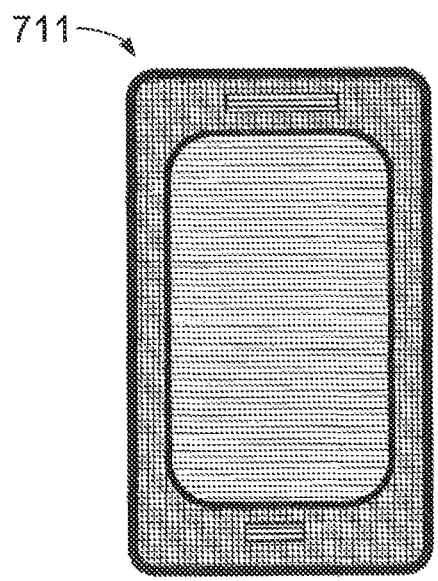
FIG. 7C illustrates a front view of a case for a portable electronic device according to some embodiments of the present disclosure.
Figure 7D:
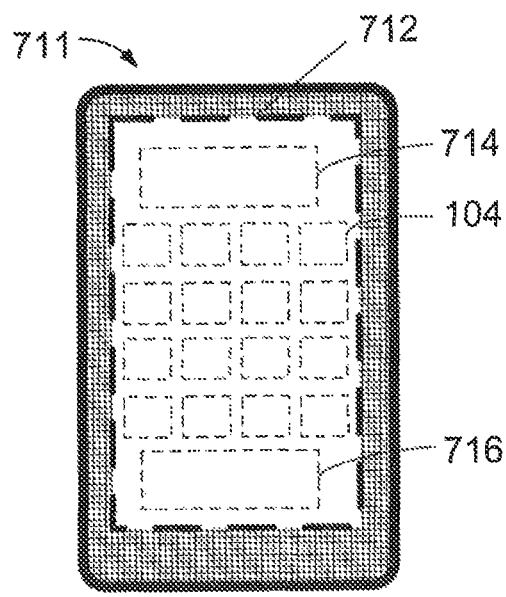
FIG. 7D illustrates a back view of a case including imaging elements for a portable electronic device according to some embodiments of the present disclosure.

FIG. 7C illustrates a front view of a case 711 for as portable electronic device according to some embodiments of the present disclosure. FIG. 7D illustrates a back view of the case 711 including imaging elements for a portable electronic device according to some embodiments of the present disclosure. The case 711 may be configured to at least partially enclose the portable electronic device 700. In some embodiments, case 711 may simultaneously provide imaging capabilities to portable electronic device 700 and serve as a protective case. The case may be made of any suitable material such as rubber, plastic, leather, and/or the like. As shown in FIG. 71D, an imaging circuit 712. (e.g., an integrated circuit) may be provided on (e.g., directly on), embedded in, and/or otherwise coupled to the back surface and/or other surface(s) of the case 711. Case 711 may be considered part of portable electronic device 700.

The imaging circuit 712 may include one or more imaging elements 104. As discussed above, the imaging elements 104 may include sources and/or sensors. The imaging circuit 712 may also include a communication device 714 configured to communicate with the portable electronic device 700 via a wired or wireless link. For example, the imaging circuit 712 may include a communication transmitter/receiver which utilizes an infrared signal, a Bluetooth communication signal, a near-field communication signal, and/or the like to communicate with the portable electronic device 700. In some embodiments, the communication device 714 may be in communication with the processing circuitry of a portable electronic device through a wired communications link (e.g., a USB port, or other data port), or combination of wired and wireless links. In some embodiments, the imaging circuit 712 may receive power through wired and/or wireless connection(s) to the portable electronic device. In some embodiments, the imaging circuit 712 may receive power from a separate power source (e.g., a battery) that is coupled to the imaging circuit 712. In some embodiments, when the portable electronic device 700 is coupled to or attached to the case 711, a software application and/or drivers are automatically loaded and/or executed by the portable electronic device 700 in order to render an image based on communication with the imaging circuit 712. The software application and/or drivers may be stored in a memory of the imaging circuit 712 and communicated to the portable electronic device 700 and/or may be retrieved by the portable electronic device through a network (e.g., the internet).

In some embodiments, the portable electronic device 700 receives raw data from the communication device 714 and processes the raw data using processing circuitry (e.g., image signal processor, digital signal processor, filters, and/or the like) included. In the portable electronic device 700. In some embodiments, the imaging circuit 712 includes a local imaging processor 716 configured to process signals received by imaging elements 104. The communication device 714 may be configured to communicate data received from the imaging elements 104 (e.g., such as raw sensor data) and/or may communicate processed data that is received from the local imaging processor 716. As shown in FIG. 7A, the portable electronic device 700 includes an interface 702 for displaying an image that is rendered by processing signals received from the communication device 714.

Figure 8A:
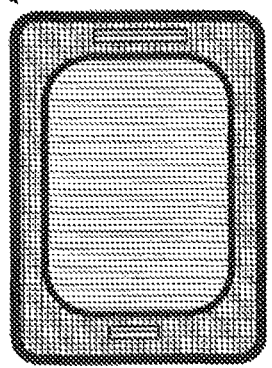
FIG. 8A illustrates a front view of a case for a portable electronic device according to some embodiments of the present disclosure.
Figure 8B:
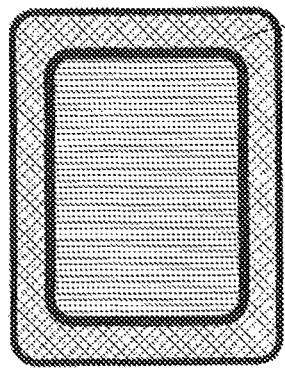
FIG. 8B illustrates a back view of a case including a retaining mechanism for a modular unit utilized with a portable electronic device according to some embodiments of the present disclosure.
Figure 8C:
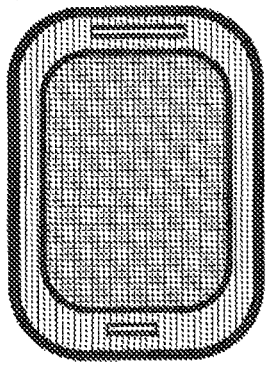
FIG. 8C illustrates a front view of a case for a portable electronic device according to some embodiments of the present disclosure.
Figure 8D:
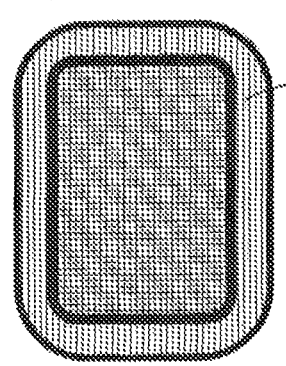
FIG. 8D illustrates a back view of a case including a retaining mechanism for a modular unit utilized with a portable electronic device according to some embodiments of the present disclosure.
Figure 8E:
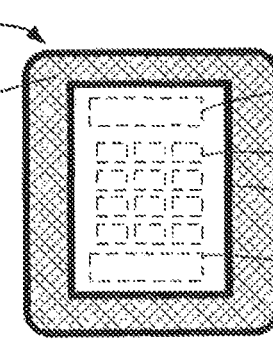
FIG. 8E illustrates a modular unit including an imaging circuit according to some embodiments of the present disclosure.

In some embodiments, an imaging circuit (e.g., an integrated circuit) may be provided separately such that it can be mounted and/or attached to different cases used by different portable electronic devices. FIG. 8A illustrates a front view of a case 811A for a portable electronic device according to some embodiments of the present disclosure. FIG. 8B illustrates a back view of the case 811A including a retaining mechanism 820 for a modular unit 830 utilized with a portable electronic device according to some embodiments of the present disclosure. FIG. 8C illustrates a front view of a case 811B for a portable electronic device according to some embodiments of the present disclosure. FIG. 8D illustrates a back view of the case 811B including a retaining mechanism for a modular unit 830 utilized with a portable electronic device according to some embodiments of the present disclosure. FIG. 8E illustrates a modular unit 830 including an imaging circuit 712 according to some embodiments of the present disclosure. As shown in FIGS. 8A-8D, the case 811A has a different shape than the case 811B. The case 811A may be utilized for a first portable electronic device, while the case 811B may be utilized for a second portable electronic device having a different size and/or shape than the first portable electronic device. Each of the cases 811A and 811B includes a retaining mechanism 820 that is configured to retain the modular unit 830.

The modular unit 830 may include the imaging circuit 712 as discussed above with reference to FIGS. 7A-7D. The imaging circuit 712 may include one or more imaging elements 104, a communication device 714, and/or a local imaging processor 716. The modular unit 830 also includes a coupling mechanism 832 that is configured to engage with the retaining mechanism 820 of the cases 811A and 811B. For example, in some embodiments, the retaining mechanism 820 may correspond to a slot on the case 811A and/or 811B that is configured to receive the modular unit 830. The coupling mechanism 832 may be shaped to correspond to the slot of the case 811A and/or 811B such that the modular unit 830 may be secured by the case 811A and/or 811B. In some embodiments, the retaining mechanism 820 and the coupling mechanism 832 may include corresponding structures for locking the modular unit 830 in place during use. In some embodiments, the retaining mechanism 820 may include one or more magnets having a first polarity, and the coupling mechanism 832 may include one or more magnets having a second polarity that is opposite of the first polarity such that the modular unit 830 can be retained by the case 811A and/or 811B.

As described with reference to FIGS. 8A-8E, since the modular unit 830 may be incorporated with different cases 811A and/or 811B that are utilized for different portable electronic devices, the modular unit 830 may advantageously provide flexibility in the incorporation of an imaging system with different portable electronic devices. Furthermore, different cases 811A and 811B may be manufactured using any suitable techniques (e.g., 3-D printing, injection molding, or the like). In some embodiments, case 811A and/or case 811B may be manufactured at low cost such that the different cases 811A and 811B may be discarded and/or upgraded while remaining compatible with the modular unit 830. As a result, the modular unit 830 can be integrated into and utilized by a user with a plurality of portable electronic devices even when the design of the portable electronic devices is changed (e.g., updated and/or upgraded).

Examples of suitable imaging devices that may integrated within or coupled to a portable electronic device according to some embodiments of the present disclosure are described in commonly-owned U.S. patent application Ser. No. 13/654,337 filed Oct. 17, 2012, and entitled "Transmissive Imaging and Related Apparatus and Methods;" U.S. Provisional Application Ser. No. 61/798,851 filed Mar. 15, 2013, and entitled "Monolithic Ultrasonic Imaging Devices, Systems and Methods;" and U.S. Provisional Application Ser. No. 61/794,744 filed on Mar. 15, 2013, and entitled "Complementary Metal Oxide Semiconductor (CMOS) Ultrasonic. Transducers and Methods for Forming the Same," each of which is incorporated by reference in its entirety.

Having thus described several aspects and embodiments of the technology described herein, it is to be appreciated that various alterations, modifications, and improvements will readily occur to those skilled in the art. Such alterations, modifications, and improvements are intended to be within the spirit and scope of the technology described in the present disclosure. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a non-transitory computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program, modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed. In an order different than illustrated, which may include performing some acts simultaneously, even though shown as sequential acts in illustrative embodiments.

All definitions, as defined and used herein, should be understood to control over dictionary definitions and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A non-invasive integrated portable electronic device, comprising:
    a single housing containing:
    at least one imaging element being integrated into the housing, the at least one imaging element receives at least one radiation signal;
    at least one processing element being integrated into the housing and being communicatively coupled with the at least one imaging element, the at least one processing element processes the at least one received radiation signal;
    a display being integrated into the housing and being communicatively coupled with the at least one processing element,
    the at least one processing element, based on the at least one received processed radiation signal,
    identifies, based on an analysis of the at least one received processed radiation signal and a comparison to data stored in a memory of the portable electronic device, at least one part of an interior portion of a subject;
    renders on the display a continuous three-dimensional polarized, exploded, real-time image, upwardly projects, using the display, the image from a surface of the display,
    simulates, based on the rendered image, a virtual window into the interior portion of the subject while the portable electronic device, including the housing containing the at least one imaging element, the at least one processing element and the display, are directed at the subject and being positioned remotely and within approximately one meter from the subject and without any part of the portable electronic device contacting the subject, the virtual window containing identification information of the at least one part of the interior portion of the subject,
    provides, using the simulated virtual window, a projected view of the interior portion of the subject allowing a user of the non-invasive portable electronic device to look inside the subject, and simulates an updated virtual window into the interior portion of the subject corresponding to a new position of the non-invasive portable electronic device in relation to the subject;
    wherein
    the at least one processor generates the identification information for display in the window based on information stored in the memory of the portable electronic device;
    the information includes data associated with one or more abnormalities in an imaged structure or object.

2. The portable electronic device according to claim 1, wherein the image changes to display at least another interior portion of the subject as the electronic portable device, including the display, is moved relative to the subject.

3. The portable electronic device according to claim 1, wherein the at least one radiation signal is being received by the at least one imaging element after being reflected from the subject.

4. The portable electronic device according to claim 1, wherein the at least one radiation signal is being received by the at least one imaging element after passing through the subject.

5. The portable electronic device according to claim 1, wherein the at least one radiation signal is an ultrasound signal.

6. The portable electronic device according to claim 1, further comprising:
    a plurality of imaging elements configured to receive a plurality of radiation signals; and
    a plurality of processors, communicatively coupled to the plurality of imaging signals, the plurality of processors configured to process the received plurality of radiation signals;
    wherein the plurality of processors render the window on the display containing the real-time image of the portion of the interior of the subject.

7. The portable electronic device according to claim 1, wherein a movement of the portable electronic device, including the display, while being directed at the subject, causes rendering of an updated real-time image of another portion of the interior of the subject in the window on the display.

8. The portable electronic device according to claim 7, wherein the real-time image is continuously updated during the movement of the portable electronic device, including the display.

9. The portable electronic device according to claim 1, wherein the at least one imaging element includes a transducer.

10. The portable electronic device according to claim 9, wherein the transducer is an ultrasound transducer.

11. The portable electronic device according to claim 1, wherein the image is adjusted based on at least one of the following input parameters: a zoom level, a centering position, a level of detail, a depth of the interior portion, a resolution, a brightness, a color, and any combination thereof.

12. The portable electronic device according to claim 1, wherein the identification information includes at least one of the following: text and graphics.

13. The portable electronic device according to claim 1, wherein the information includes data associated with at least one of the following: an organ, artery, vein, tissue, bone, and other bodily content or part.

14. The portable electronic device according to claim 1, wherein the information includes data associated with at least one of the following: a shape, color, texture, cellular characteristic, and tissue characteristic of an imaged structure or object.

15. The portable electronic device according to claim 1, wherein the subject includes at least one of the following: a human body and a portion of a human body.

16. The portable electronic device according to claim 1, further comprising at least one radiation sensor, the at least one radiation sensor being communicatively coupled to the at least one processing element;
wherein the at least one radiation sensor receives radiation reflected by or passing through the subject;
wherein the at least one processing element renders the real-time image based at least in part on the radiation received by the at least one radiation sensor.

17. A method for imaging an interior portion of a subject using a non-invasive integrated portable electronic device, the portable electronic device including
a single housing containing:
at least one imaging element being integrated into the housing;
at least one processing element being integrated into the housing and being communicatively coupled with the at least one imaging element, and
a display being integrated into the housing and being communicatively coupled with the at least one processing element;
the method comprising:
positioning the portable electronic device remotely and within approximately one meter away from the subject and without any part of the portable electronic device contacting the subject;
receiving, using the at least one imaging element, at least one radiation signal;
processing, using the at least one processing element, the at least one received radiation signal;
rendering, using the at least one processing element, based on the at least one received processed radiation signal, on the display a continuous three-dimensional polarized, exploded, real-time image;
upwardly projecting, using the display, the image from a surface of the display;
simulating, using the at least one processing element, based on the rendered image, a virtual window into an interior portion of a subject while the portable electronic device, including the housing containing the at least one imaging element, the at least one processing element and the display, are directed at the subject;
providing, using a simulated virtual window, a projected view of the interior portion of the subject and allowing a user of the portable electronic device to look inside the subject;
simulating an updated virtual window into the interior portion of the subject corresponding to a new position of the non-invasive portable electronic device in relation to the subject; and
identifying, using the at least one processing element, based on an analysis of the at least one received processed radiation signal and a comparison to data stored in a memory of the portable electronic device, at least one part of the interior portion and displaying, using the display, in the virtual window
at least one identification information associated with the identified at least one part of the interior portion, and
data indicating at least one abnormality associated with the identified at least one part of the interior portion.

18. A non-invasive integrated portable electronic device, comprising:
a single housing containing:
at least one imaging element being integrated into the housing, the at least one imaging element receives at least one radiation signal, the at least one imaging element including at least one ultrasound transducer and the at least one radiation signal being an ultrasound signal;
at least one processing element being integrated into the housing and being communicatively coupled with the at least one imaging element, the at least one processing element processes the at least one received radiation signal; and
a display being integrated into the housing and being communicatively coupled with the at least one processing element,
the at least one processing element, based on the at least one received processed radiation signal,
renders on the display a continuous three-dimensional polarized, exploded, real-time image,
upwardly projects, using the display, the image from a surface of the display,
simulates, based on the rendered image, a virtual window into an interior portion of a subject while the portable electronic device, including the display, is directed at the subject,
provides, using the simulated virtual window, a projected view of the interior portion of the subject to allow a user of the non-invasive portable electronic device to look inside the subject,
simulates an updated virtual window into the interior portion of the subject corresponding to a new position of the non-invasive portable electronic device in relation to the subject;
wherein the image is rendered while the portable electronic device, including the housing containing the at least one imaging element, the at least one processing element and the display, are positioned remotely and within approximately one meter from the subject and without any part of the portable electronic device contacting the subject; and
identifies, based on an analysis of the at least one received processed radiation signal and a comparison to data stored in a memory of the portable electronic device, at least one part of the interior portion and displays in the virtual window
at least one identification information associated with the identified at least one part of the interior portion, and
data indicating at least one abnormality associated with the identified at least one part of the interior portion.

* * * * *